(12) United States Patent
Chen et al.

(10) Patent No.: US 10,407,449 B1
(45) Date of Patent: Sep. 10, 2019

(54) FLAME RETARDANT, PRECURSOR THEREOF, AND FLAME RETARDANT MATERIAL

(71) Applicant: X-EXTREME PTE. LTD., Taichung (TW)

(72) Inventors: Yun-Chi Chen, Taichung (TW); Chun-Yang Yang, Tainan (TW); Sheng-You Lin, Nanzhou Township (TW)

(73) Assignee: X-EXTREME PTE. LTD., Taichung (TW)

( * ) Notice: Subject to any disclaimer, the term of this patent is extended or adjusted under 35 U.S.C. 154(b) by 0 days.

(21) Appl. No.: 16/008,385

(22) Filed: Jun. 14, 2018

(30) Foreign Application Priority Data

Jun. 13, 2018 (TW) .............................. 107120287 A

(51) Int. Cl.
*C09K 21/12* (2006.01)
*C08K 5/5313* (2006.01)
*C07F 9/6571* (2006.01)

(52) U.S. Cl.
CPC ...... *C07F 9/657172* (2013.01); *C08K 5/5313* (2013.01); *C09K 21/12* (2013.01)

(58) Field of Classification Search
None
See application file for complete search history.

(56) References Cited

U.S. PATENT DOCUMENTS 5,594,046 A    1/1997 Joachimi

FOREIGN PATENT DOCUMENTS

CN          103865025 A       6/2014

OTHER PUBLICATIONS

STN Registry database entry for CAS RN 92383-90-9, STN Entry Date Dec. 17, 1984, Accessed Jan. 7, 2019.*

* cited by examiner

*Primary Examiner* — Alicia L Otton
(74) *Attorney, Agent, or Firm* — Birch, Stewart, Kolasch & Birch, LLP

(57) ABSTRACT

A flame retardant is provided, which has a structure represented by the following Structural Formula (I) or (II):

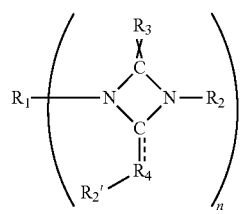

Structural Formula (I)

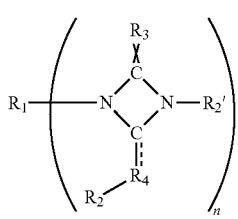

Structural Formula (II)

wherein $R_1$ and $R_2$ each independently represent a substituted or unsubstituted aromatic group, a substituted or unsubstituted araliphatic group, a substituted or unsubstituted aliphatic group, or a substituted or unsubstituted cycloaliphatic group; $R_2$ is $R_2\text{-}(\text{N}=\text{C}=\text{N}-R_5\text{-})_m$, wherein $R_5$ is arylene or alkylene, and is identical or different in the repeat unit, and m is an integer from 0 to 5; n is an integer equal to or larger than 1; "⤬" and "═" respectively represent either a double bond or two single bonds, and "⤬" and "═" are not both double bonds; when "⤬" represents a double bond, $R_3$ is an oxygen atom; when "⤬" represents two single bonds, $R_3$ is $R_{3a}$ and $R_{3b}$, in which $R_{3a}$ is a hydroxyl group and $R_{3b}$ is

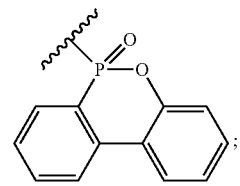

when "═" represents a double bond, $R_4$ is a nitrogen atom; when "═" represents two single bonds, $R_4$ is $R_{4a}$ and $R_{4b}$, in which $R_{4a}$ is a secondary amino group and $R_{4b}$ is

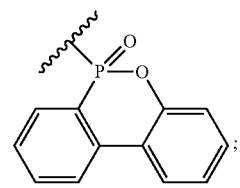

and $R_2'$ is attached to $R_{4a}$ in Structural Formula (I), and $R_2$ is attached to $R_{4a}$ in Structural Formula (II).

10 Claims, 19 Drawing Sheets

FLAME RETARDANT, PRECURSOR THEREOF, AND FLAME RETARDANT MATERIAL

BACKGROUND OF THE DISCLOSURE

1. Field of the Invention

The present disclosure relates generally to a flame retardant and more particularly, to a flame retardant having a reactive functional group.

2. Description of the Related Art

Polymer materials, such as epoxy resins, are widely used in industry because of their good electrical properties, high temperature resistance, chemical resistance, dimensional stability, and high adhesiveness. For example, epoxy resins can be used as protective coatings, encapsulating materials for integrated circuits or adhesives, and the like.

In order to improve the flame retardancy of a polymer, an additive-type flame retardant or a reactive flame retardant is generally introduced into the polymer by adding to or reacting with the polymer.

An additive-type flame retardant, for example, a halogen-containing flame retardant such as tetrabromobisphenol A (TBBA) is added to the polymer. However, the halogen-containing flame retardants release harmful substances such as dioxin/furan during combustion, so they are not environmentally friendly. In addition, since the additive-type flame retardant is added to the polymer by mixing therewith, the following problems are present.

1. When the flame retardant is added in an insufficient amount or mixed unevenly, the flame retardancy of the polymer is poor.

2. When an excess of flame retardant is added, the mechanical properties of the polymer is deteriorated.

The reactive flame retardant reacts with certain functional groups of or forms an intermolecular force with the polymer, to improve the compatibility of the flame retardant with the polymer, so that the polymer is allowed to have a better flame retardancy. For example, an inherent flame-retardant rigid polyurethane foam is disclosed in Chinese Patent No. CN103865025A, in which a DOPO-HB flame retardant containing two reactive hydroxyl groups (9, 10-dihydro-9-oxa-10-phosphaphenanthrene-4-hydroxybenzyl alcohol) is used.

However, since the existing reactive flame retardant has only one kind of reactive functional group (i.e. hydroxyl group), the applicability thereof is limited.

SUMMARY OF THE DISCLOSURE

In view of the foregoing, an objective of the present disclosure is to provide a flame retardant having at least one kind of reactive functional group, which has superior flame retardancy and is environmentally friendly.

To achieve the above objective, the present disclosure provides a flame retardant having a structure represented by the following Structural Formula (I) or (II).

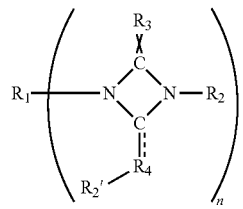

Structural Formula (I)

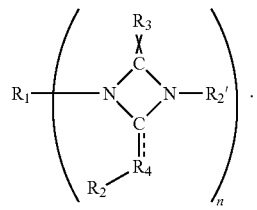

Structural Formula (II)

In Structural Formulas (I) and (II), $R_1$ and $R_2$ each independently represent a substituted or unsubstituted aromatic group, a substituted or unsubstituted araliphatic group, a substituted or unsubstituted aliphatic group or a substituted or unsubstituted cycloaliphatic group, $R_2'$ is $R_2$—$(\!-\!N\!=\!C\!=\!N\!-\!R_5\!-\!)_m$, in which $R_5$ is arylene or alkylene and is identical or different in the repeat unit, and m is an integer from 0 to 5; n is an integer equal to or larger than 1; "⤻" and "⸺" respectively represent either a double bond or two single bonds, and "⤻" and "⸺" are not both double bonds; when "⤻" represents a double bond, $R_3$ is an oxygen atom; when "⤻" represents two single bonds, $R_3$ is $R_{3a}$ and $R_{3b}$, in which $R_{3a}$ is a hydroxyl group, and $R_{3b}$ is

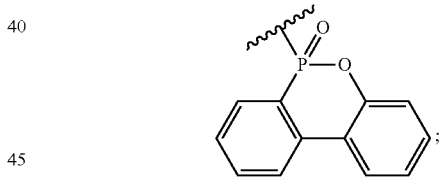

when "⸺" represents a double bond, $R_4$ is a nitrogen atom; when "⸺" represents two single bonds, $R_4$ is $R_{4a}$ and $R_{4b}$, in which $R_{4a}$ is a secondary amino group, and $R_{4b}$ is

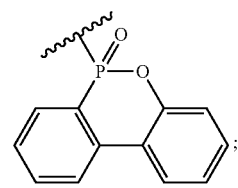 [SMILES: *P1(=O)Oc2ccccc2-c2ccccc21]

and $R_2'$ is attached to $R_{4a}$ in Structural Formula (I), and $R_2$ is attached to $R_{4a}$ in Structural Formula (II).

In the present disclosure, in Structural Formulas (I) and (II), n is an integer from 1 to 4. Preferably, n is an integer from 1 to 3.

In the present disclosure, in Structural Formulas (I) and (II), $R_1$ may be a substituted or unsubstituted aryl or aralkyl group having 6 to 20 carbon atoms, a substituted or unsubstituted alkyl group having 1 to 18 carbon atoms, or a substituted or unsubstituted cycloalkyl group having 6 to 16 carbon atoms; preferably a substituted or unsubstituted aryl group having 6 to 18 carbon atoms, a substituted or unsubstituted aralkyl group having 6 to 15 carbon atoms, a substituted or unsubstituted alkyl group having 1 to 10 carbon atoms, or a substituted or unsubstituted cycloalkyl group having 6 to 10 carbon atoms; and more preferably an unsubstituted aryl group having 6 to 14 carbon atoms, an unsubstituted aralkyl group having 6 to 13 carbon atoms, an unsubstituted alkyl group having 1 to 6 carbon atoms, or an unsubstituted cycloalkyl group having 6 to 8 carbon atoms.

In the present disclosure, in Structural Formulas (I) and (II), $R_2$ may be a substituted or unsubstituted aryl or aralkyl group having 6 to 20 carbon atoms, a substituted or unsubstituted alkyl group having 1 to 18 carbon atoms, or a substituted or unsubstituted cycloalkyl group having 6 to 16 carbon atoms; preferably a substituted or unsubstituted aryl group having 6 to 18 carbon atoms, a substituted or unsubstituted aralkyl group having 6 to 15 carbon atoms, a substituted or unsubstituted alkyl group having 1 to 10 carbon atoms, or a substituted or unsubstituted cycloalkyl group having 6 to 10 carbon atoms; and more preferably an unsubstituted aryl group having 6 to 14 carbon atoms, an unsubstituted aralkyl group having 6 to 13 carbon atoms, an unsubstituted alkyl group having 1 to 6 carbon atoms, or an unsubstituted cycloalkyl group having 6 to 8 carbon atoms.

In the present disclosure, in Structural Formulas (I) and (II), $R_5$ may be an alkylene group having 1 to 24 carbon atoms or an arylene group having 6 to 22 carbon atoms.

Another object of the present disclosure is to provide a precursor for preparing the flame retardant as described above, which has a structure represented by the following Structural Formula (III) or (IV).

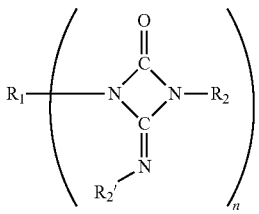
Structural Formula (III)

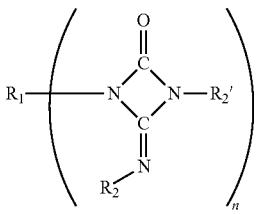
Structural Formula (IV)

In Structural Formulas (III) and (IV), $R_1$ and $R_2$ each independently represent a substituted or unsubstituted aromatic group, a substituted or unsubstituted araliphatic group, a substituted or unsubstituted aliphatic group, or a substituted or unsubstituted cycloaliphatic group; $R_2'$ is $R_2$—(N=C=N—$R_5$)$_m$, in which $R_5$ is arylene or alkylene and is identical or different in the repeat unit, and m is an integer from 0 to 5; and n is an integer equal to or larger than 1.

In the present disclosure, in Structural Formulas (III) and (IV), n is an integer from 1 to 4. Preferably, n is an integer from 1 to 3.

In the present disclosure, in Structural Formulas (III) and (IV), $R_1$ may be a substituted or unsubstituted aryl or aralkyl group having 6 to 20 carbon atoms, a substituted or unsubstituted alkyl group having 1 to 18 carbon atoms, or a substituted or unsubstituted cycloalkyl group having 6 to 16 carbon atoms; preferably a substituted or unsubstituted aryl group having 6 to 18 carbon atoms, a substituted or unsubstituted aralkyl group having 6 to 15 carbon atoms, a substituted or unsubstituted alkyl group having 1 to 10 carbon atoms, or a substituted or unsubstituted cycloalkyl group having 6 to 10 carbon atoms; and more preferably an unsubstituted aryl group having 6 to 14 carbon atoms, an unsubstituted aralkyl group having 6 to 13 carbon atoms, an unsubstituted alkyl group having 1 to 6 carbon atoms, or an unsubstituted cycloalkyl group having 6 to 8 carbon atoms.

In the present disclosure, in Structural Formulas (III) and (IV), $R_2$ may be a substituted or unsubstituted aryl or aralkyl group having 6 to 20 carbon atoms, a substituted or unsubstituted alkyl group having 1 to 18 carbon atoms, or a substituted or unsubstituted cycloalkyl group having 6 to 16 carbon atoms; preferably a substituted or unsubstituted aryl group having 6 to 18 carbon atoms, a substituted or unsubstituted aralkyl group having 6 to 15 carbon atoms, a substituted or unsubstituted alkyl group having 1 to 10 carbon atoms, or a substituted or unsubstituted cycloalkyl group having 6 to 10 carbon atoms; and more preferably an unsubstituted aryl group having 6 to 14 carbon atoms, an unsubstituted aralkyl group having 6 to 13 carbon atoms, an unsubstituted alkyl group having 1 to 6 carbon atoms, or an unsubstituted cycloalkyl group having 6 to 8 carbon atoms.

In the present disclosure, in Structural Formulas (III) and (IV), $R_5$ may be an alkylene group having 1 to 24 carbon atoms or an arylene group having 6 to 22 carbon atoms.

Since the flame retardant of the present disclosure has at least one kind of reactive functional group selected from hydroxyl group (OH group) and amino group (NH group), or has both of the foregoing reactive functional groups, in addition to a compound/polymer capable of reacting with the OH group, the flame retardant of the present disclosure can react with a compound/polymer capable of reacting with the NH group, thus expanding the applicability of the flame retardant of the present disclosure. Further, after the flame retardant of the present disclosure is mixed and polymerized with a polymer, the cured polymer can achieve a flame retardancy of UL-94 V0.

DETAILED DESCRIPTION OF THE DISCLOSURE

Figure 1:
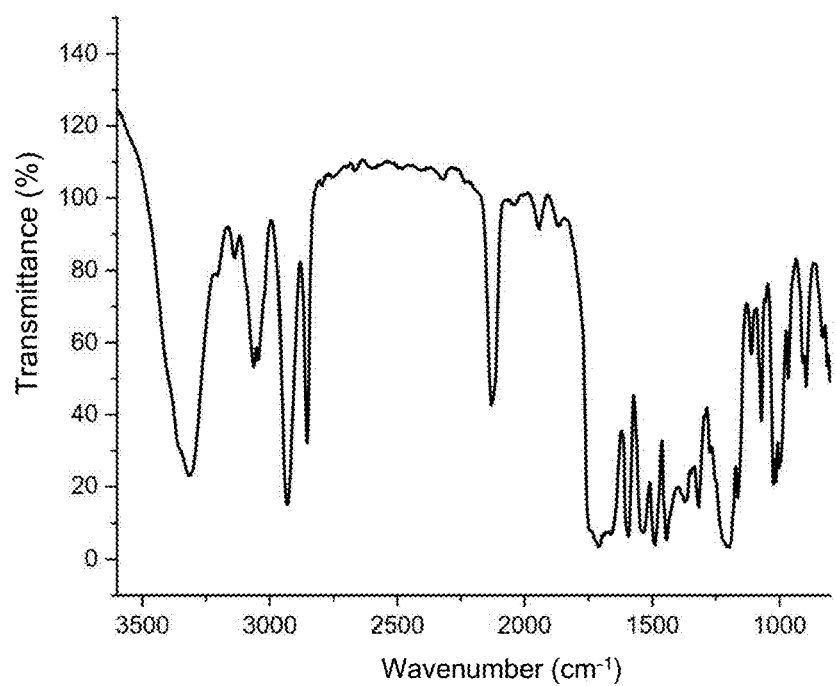
FIGS. 1 to 11 are FT-IR spectra of precursors 1 to 11 obtained in Examples 1 to 11 of the present disclosure, respectively.

To better understand the present disclosure, the present disclosure is now described in greater detail with reference to the following experimental examples and the accompanying drawings. It is to be understood that the following embodiments and experimental examples are merely illustrative of the present disclosure and are not intended to limit the present disclosure.

The present disclosure provides a halogen-free phosphorous-containing flame retardant having at least one kind of reactive functional group. The flame retardant has a structure represented by the following Structural Formula (I) or (II).

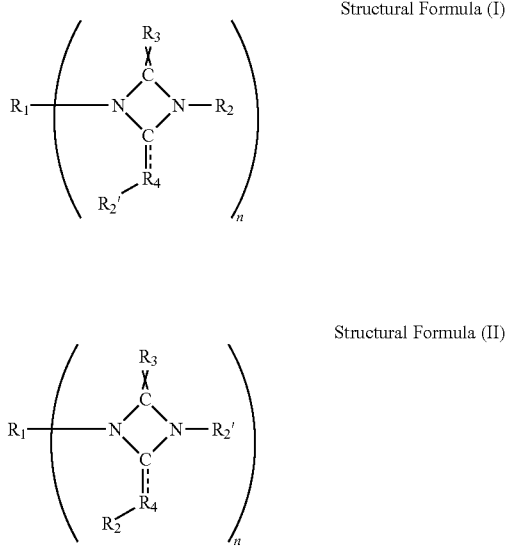

Structural Formula (I)

Structural Formula (II)

In Structural Formula (I) or (II), $R_1$ and $R_2$ each independently represent a substituted or unsubstituted aromatic group, a substituted or unsubstituted araliphatic group, a substituted or unsubstituted aliphatic group, or a substituted or unsubstituted cycloaliphatic group; $R_2{}'$ is $R_2$—( N=C=N—$R_5$ )$_m$, in which $R_5$ is arylene or alkylene and is identical or different in the repeat unit, and m is an integer from 0 to 5; n is an integer equal to or larger than 1; "⚍" and "⚌" respectively represent either a double bond or two single bonds, and "⚍" and "⚌" are not both double bonds; when "⚍" represents a double bond, $R_3$ is an oxygen atom; when "⚍" represents two single bonds, $R_3$ is $R_{3a}$ and $R_{3b}$, in which $R_{3a}$ is a hydroxyl group, and $R_{3b}$ is

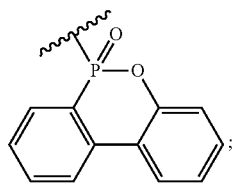 [SMILES: *P1(=O)Oc2ccccc2-c2ccccc21]

when "⚌" represents a double bond, $R_4$ is a nitrogen atom; when "⚌" represents two single bonds, $R_4$ is $R_{4a}$ and $R_{4b}$, in which $R_{4a}$ is a secondary amino group, and $R_{4b}$ is

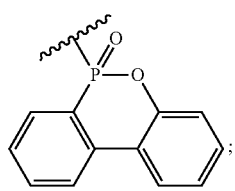 [SMILES: *P1(=O)Oc2ccccc2-c2ccccc21]

and $R_2{}'$ is attached to $R_{4a}$ in Structural Formula (I), and $R_2$ is attached to $R_{4a}$ in Structural Formula (II).

In Structural Formula (I) or (II), n may be an integer from 1 to 4, preferably an integer from 1 to 3, and more preferably an integer from 1 to 2.

In Structural Formula (I) or (II), $R_1$ may be a substituted or unsubstituted aryl or aralkyl group having 6 to 20 carbon atoms, a substituted or unsubstituted alkyl group having 1 to 18 carbon atoms, or a substituted or unsubstituted cycloalkyl group having 6 to 16 carbon atoms; preferably a substituted or unsubstituted aryl group having 6 to 18 carbon atoms, a substituted or unsubstituted aralkyl group having 6 to 15 carbon atoms, a substituted or unsubstituted alkyl group having 1 to 10 carbon atoms, or a substituted or unsubstituted cycloalkyl group having 6 to 10 carbon atoms; and more preferably an unsubstituted aryl group having 6 to 14 carbon atoms, an unsubstituted aralkyl group having 6 to 13 carbon atoms, an unsubstituted alkyl group having 1 to 6 carbon atoms, or an unsubstituted cycloalkyl group having 6 to 8 carbon atoms.

In Structural Formula (I) or (II), $R_2$ may be a substituted or unsubstituted aryl or aralkyl group having 6 to 20 carbon atoms, a substituted or unsubstituted alkyl group having 1 to 18 carbon atoms, or a substituted or unsubstituted cycloalkyl group having 6 to 16 carbon atoms; preferably a substituted or unsubstituted aryl group having 6 to 18 carbon atoms, a substituted or unsubstituted aralkyl group having 6 to 15 carbon atoms, a substituted or unsubstituted alkyl group having 1 to 10 carbon atoms, or a substituted or unsubstituted cycloalkyl group having 6 to 10 carbon atoms; and more preferably an unsubstituted aryl group having 6 to 14 carbon atoms, an unsubstituted aralkyl group having 6 to 13 carbon atoms, an unsubstituted alkyl group having 1 to 6 carbon atoms, or an unsubstituted cycloalkyl group having 6 to 8 carbon atoms.

In Structural Formula (I) or (II), $R_5$ may be an alkylene group having 1 to 24 carbon atoms or an arylene group having 6 to 22 carbon atoms.

As used in the specification, the term "aryl group" means a monovalent monocyclic or bicyclic aromatic hydrocarbon group, which may contain a heteroatom such as nitrogen, oxygen, or sulfur, etc., including specifically, but not limited to, phenyl group, tolyl group, xylyl group, ethylphenyl group, naphthyl group, biphenyl group, and the like. The term "aralkyl group" means a $R^aR^b$ group, in which $R^a$ is alkylene and $R^b$ is aryl, and which may contain a heteroatom such as nitrogen, oxygen, or sulfur, etc., including specifically, but not limited to, benzyl group, 2-phenylethyl group, 3-phenylpropyl group, and the like. The term "alkyl group" means a straight or branched saturated monovalent hydrocarbon group, which may contain a heteroatom such as nitrogen, oxygen, or sulfur, etc., including specifically, but not limited to, methyl group, ethyl group, n-propyl group, iso-propyl group, 1-methylpropyl group, 2-methylpropyl group, n-butyl group, iso-butyl group, 1-methylbutyl group, 2-methylbutyl group, pentyl group, hexyl group, heptyl group, octyl group, and the like. The term "cycloalkyl group" means a saturated monovalent cyclic hydrocarbon group, including specifically, but not limited to, cyclohexyl group, cyclopentyl group, 4-methylcyclohexyl group, and the like. The term "arylene group" means a divalent monocyclic or bicyclic aromatic hydrocarbon group, which may contain a heteroatom such as nitrogen, oxygen, or sulfur, etc., including specifically, but not limited to, 1,2-phenylene group, 1,3-phenylene group, 1,4-phenylene group, or biphenyl-4,4'-diyl group, diphenylmethane-4,4'-diyl group, and the like. The term "alkylene group" means a straight or branched saturated divalent hydrocarbon group, including specifically, but not limited to, methylene group, ethylene group, 2,2-dimethylethylene group, propylene group, 2-methylpropylene group, butylene group, pentylene group, and the like.

The present disclosure also provides a precursor for preparing the foregoing flame retardant, which has a structure represented by the following Structural Formula (III) or (IV).

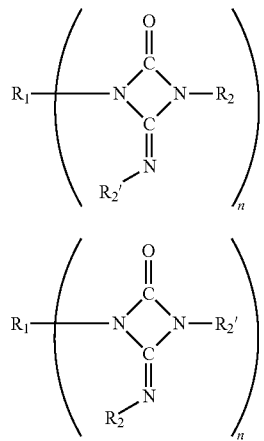

Structural Formula (III)

Structural Formula (IV)

In Structural Formula (III) or (IV), $R_1$, $R_2$, $R_5$, m and n are as defined for Structural Formula (I) or (II).

According to one embodiment of the present disclosure, the precursor represented by Structural Formula (III) or (IV) is obtained by reacting an isocyanate compound having a structural formula of $R_1$—$(N=C=O)_n$ with a carbodiimide compound having a structural formula of $R_2$—$(N=C=N—R_5—)_m N=C=N—R_2$, under a nitrogen atmosphere at a suitable reaction temperature.

Regarding the isocyanate compound having a structural formula of $R_1$—$(N=C=O)_n$, $R_1$ and n are as defined for Structural Formula (I) or (II). In the present disclosure, the isocyanate compound may be a monoisocyanate compound having only one isocyanate functional group, or a polyisocyanate compound having two to four isocyanate functional groups.

The monoisocyanate compound may be an aliphatic, aromatic or alicyclic monoisocyanate.

By way of illustration, the specific examples of the monoisocyanate compound may include, but are not limited to, methyl isocyanate, ethyl isocyanate, propyl isocyanate, isopropyl isocyanate, allyl isocyanate, butyl isocyanate, isobutyl isocyanate, sec-butyl isocyanate, tert-butyl isocyanate, n-amyl isocyanate, hexyl isocyanate, octyl isocyanate, dodecyl isocyanate, tetradecyl isocyanate, hexadecyl isocyanate, stearyl isocyanate, 3-methoxypropyl isocyanate, phenyl isocyanate, o-tolyl isocyanate, m-tolyl isocyanate, p-tolyl isocyanate, o-chlorophenyl isocyanate, m-chlorophenyl isocyanate, p-chlorophenyl isocyanate, o-ethylphenyl isocyanate, o-ethoxyphenylisocyanate, p-ethoxyphenyl isocyanate, xylyl isocyanate, benzyl isocyanate, 2,4-dichlorophenyl isocyanate, 3,4-dichlorophenyl isocyanate, 2,5-dichlorophenyl isocyanate, 1-naphthyl isocyanate, biphenyl isocyanate, phenoxyphenyl isocyanate, and cyclohexyl isocyanate.

In the present disclosure, the polyisocyanate compound may be an aliphatic, aromatic, alicyclic, araliphatic polyisocyanate or a polyisocyanate oligomer, such as a diisocyanate dimer or trimer, the structures of which are respectively as shown in Structural Formula (V) and (VI).

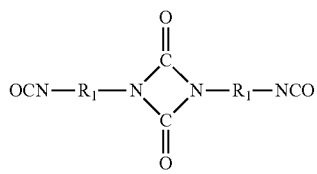

Structural Formula (V)

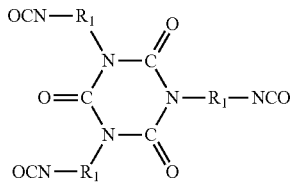

Structural Formula (VI)

By way of illustration, the specific examples of the polyisocyanate compound may include, but are not limited to, ethylene diisocyanate, propylene diisocyanate, butylene diisocyanate, pentylene diisocyanate, methylbutylene diisocyanate, hexamethylene diisocyanate (HDI), tetra-methylene diisocyanate, penta-methylene diisocyanate, heptamethylene diisocyanate, 2,2-dimethylpentane diisocyanate, 3-methoxy hexamethylene diisocyanate, octamethylene diisocyanate, m-xylylene diisocyanate, p-xylylene diisocyanate, 1,4-diethylbenzene diisocyanate, toluene-2,4-diisocyanate (TDI), naphthalene-1,4-diisocyanate, naphthalene-1,3,7-triisocyanate, diphenylmethane-2,4,4-triisocyanate, 3-methyldiphenylmethane-4,6,4'-triisocyanate, 4,4'-dimethyldiphenylmethane-2,2',5,5'-tetraisocyanate, methylene diphenyl diisocyanate (MDI), 1,2-dimethylcyclohexane diisocyanate, 1,4-dimethylcyclohexane diisocyanate, 1,3-cyclohexane diisocyanate, 1,4-cyclohexane diisocyanate, 1-methylcyclohexane-2,4-diisocyanate, isophorone diisocyanate (IPDI), tetramethylxylylene diisocyanate (TMXDI), 4,4'-dicyclohexylmethane diisocyanate (H12MDI), xylylene diisocyanate (XDI), isophorone diisocyanate dimer or trimer, hexamethylene diisocyanate trimer, and norbornene diisocyanate dimer or trimer.

Regarding the carbodiimide compound having a structural formula of $R_2\text{---}(N\text{=}C\text{=}N\text{---}R_5\text{---})_m N\text{=}C\text{=}N\text{---}R_2$, $R_2$ and m are as defined for Structural Formula (I) or (II). In the present disclosure, the carbodiimide compound may be a monocarbodiimide compound or a polycarbodiimide compound.

By way of illustration, the specific examples of the monocarbodiimide compound may include, but are not limited to, N,N'-dicyclohexylcarbodiimide (DCC), N,N'-diisopropylcarbodiimide (DIC), dimethyl carbodiimide, diisobutyl carbodiimide, dioctyl carbodiimide, diphenyl carbodiimide, naphthyl carbodiimide, and 2,2',6,6'-tetraisopropyldiphenyl carbodiimide, for example, Stabaxol® 1 sold by Rhein Chemie.

By way of illustration, the specific examples of the polycarbodiimide may include, but are not limited to, poly(dicyclohexylcarbodiimide), poly(isopropylcarbodiimide), poly(dimethylcarbodiimide), poly(diisobutylcarbodiimide), poly(dioctylcarbodiimide), poly(4,4'-diphenylmethanecarbodiimide), poly(3,3'-dimethyl-4,4'-diphenylmethanecarbodiimide), poly(tolylcarbodiimide), poly(p-phenylenecarbodiimide), poly(m-phenylenecarbodiimide), poly(1,3-diisopropylphenylenecarbodiimide), poly(1-methyl-3,5-diisopropylphenylenecarbodiimide), poly(1,3,5-triethylphenylenecarbodiimide), poly(triisopropylphenylenecarbodiimide), and poly(naphthylcarbodiimide).

For example, a commercially available carbodiimide oligomer such as CARBODILITE® V-05, V-02, V-04, V-10 and E-02 sold by Nisshinbo Chemical, and Stabaxol® P, P100, and P200 sold by Rhein Chemie, may be used.

To make those skilled in the art to fully understand the present disclosure, the present disclosure is described in more detail below with reference to the following examples and drawings, but the present disclosure is not limited thereto.

[Preparation of Precursors of Flame Retardants]

Example 1

20.1 g of dicyclohexylcarbodiimide (DCC) and 12 g of phenyl isocyanate were mixed with 20 mL of anhydrous acetone. The mixture thus obtained was placed in a dried sample container, then sealed and heated to 110° C. under continuous stirring for 7 hours. After the reaction was completed, the mixture was cooled to room temperature to produce Precursor 1 having the following structure with a yield of about 93%. Precursor 1 was characterized by FT-IR spectroscopy and the result is shown in FIG. 1. According to FIG. 1, Precursor 1 has a characteristic absorption peak (C=O or C=N) at 1720 cm$^{-1}$, and the absorption peaks observed at 2270 cm$^{-1}$ and 2154 cm$^{-1}$ are assigned to remaining unreacted isocyanate and carbodiimide residue respectively.

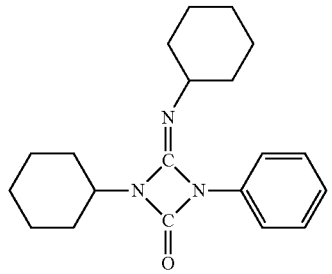

[Precursor 1]

Example 2

Figure 2:
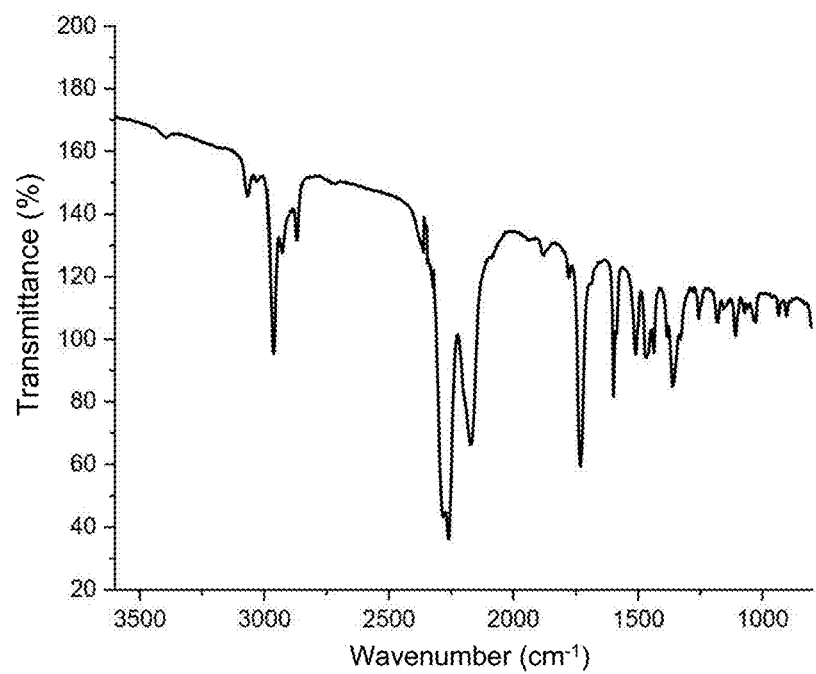

36.3 g of 2,2',6,6'-tetraisopropyldiphenylcarbodiimide (Stabaxol 1, commercially available by Rhein Chemie) and 12 g of phenyl isocyanate were mixed with 20 mL of anhydrous acetone. The mixture thus obtained was placed in a dried sample container, then sealed and heated to 110° C. under continuous stirring for 7 hours. After the reaction was completed, the mixture was cooled to room temperature to produce Precursor 2 having the following structure with a yield of about 96%. Precursor 2 was characterized by FT-IR spectroscopy and the result is shown in FIG. 2. According to FIG. 2, Precursor 2 has a characteristic absorption peak (C=O or C=N) at 1720 cm$^{-1}$, and the absorption peaks observed at 2270 cm$^{-1}$ and 2154 cm$^{-1}$ are assigned to remaining unreacted isocyanate and carbodiimide residue respectively.

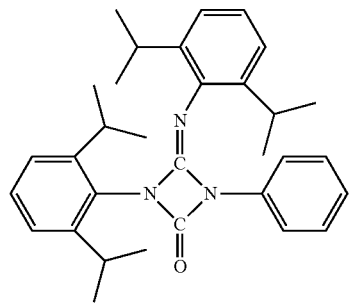

[Precursor 2]

Example 3

Figure 3:
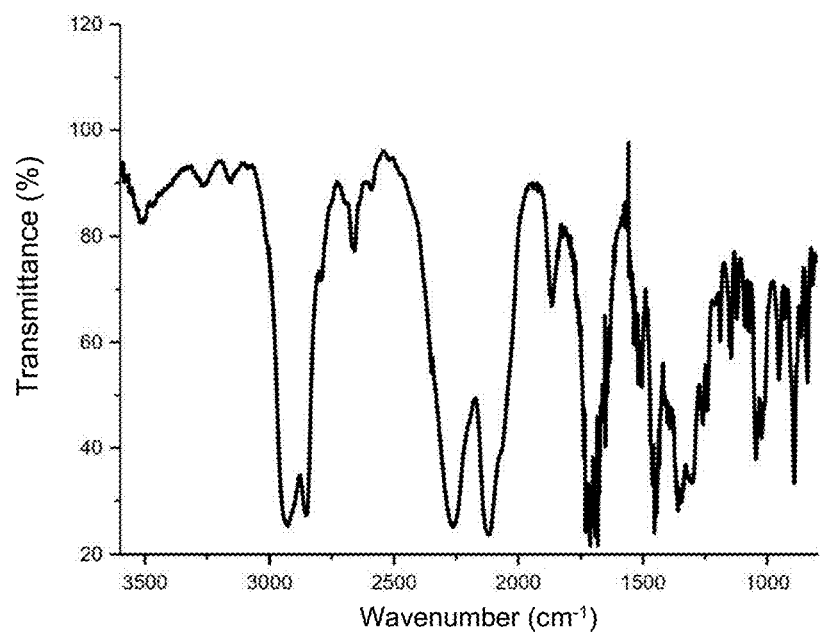

41.2 g of DCC was mixed with 16.8 g of hexamethylene diisocyanate (HDI). The mixture was added into a 500 mL three-neck flask, and toluene was then added thereto under dry nitrogen. The reaction system was heated to 110° C. under continuous stirring for 18 hours. After the reaction was completed, the mixture was cooled to room temperature. Finally, toluene was distilled out under reduced pressure to produce Precursor 3 having the following structure with a yield of more than 99%. Precursor 3 was characterized by FT-IR spectroscopy and the result is shown in FIG. 3. According to FIG. 3, Precursor 3 has a characteristic absorption peak (C=O or C=N) at 1722 cm$^{-1}$, and the absorption peaks observed at 2268 cm$^{-1}$ and 2127 cm$^{-1}$ are assigned to remaining unreacted isocyanate and carbodiimide residue respectively.

[Precursor 3]

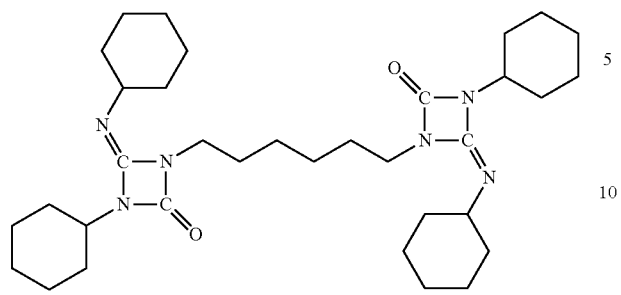

Example 4

Figure 4:
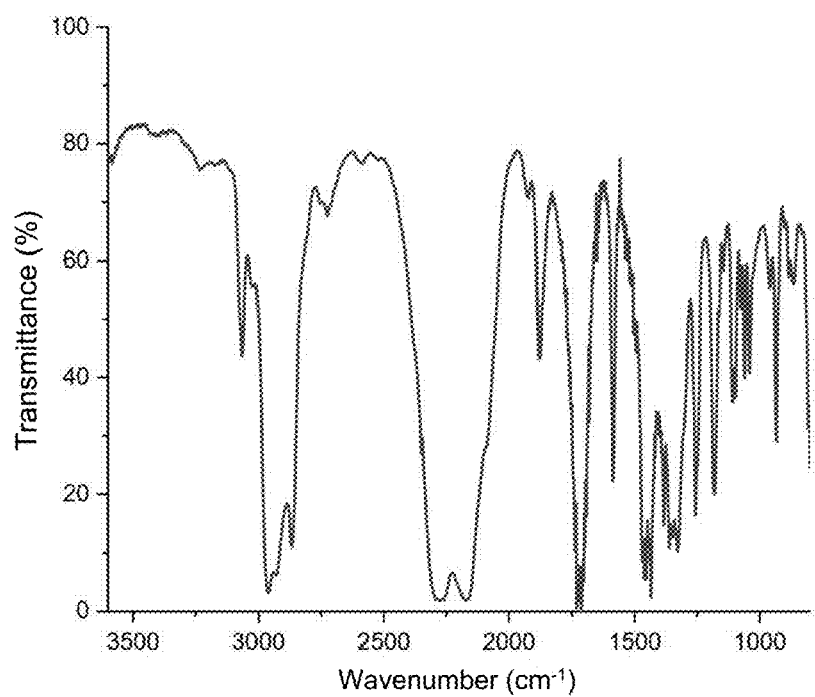

73.2 g of Stabaxol 1 was mixed with 16.8 g of HDI. The mixture was added into a 500 mL three-neck flask, and toluene was then added thereto under dry nitrogen. The reaction system was heated to 110° C. under continuous stirring for 22 hours. After the reaction was completed, the mixture was cooled to room temperature. Finally, toluene was distilled out under reduced pressure to produce Precursor 4 having the following structure with a yield of about 99%. Precursor 4 was characterized by FT-IR spectroscopy and the result is shown in FIG. 4. According to FIG. 4, Precursor 4 has a characteristic absorption peak (C=O or C=N) at 1728 $cm^{-1}$, and the absorption peaks observed at 2268 $cm^{-1}$ and 2154 $cm^{-1}$ are assigned to remaining unreacted isocyanate and carbodiimide residue respectively.

[Precursor 4]

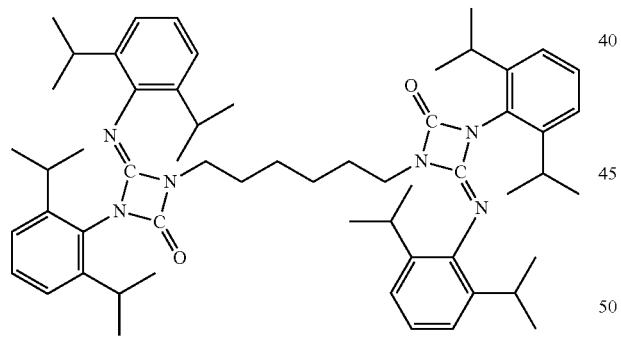

Example 5

Figure 5:
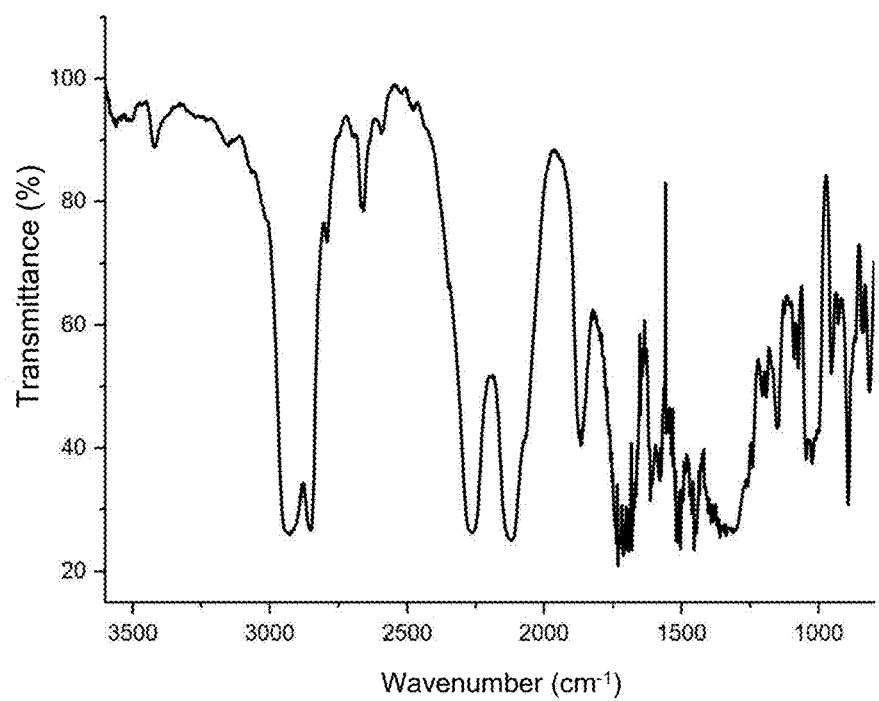

41.2 g of DCC was mixed with 17.6 g of toluene diisocyanate (TDI). The mixture was placed in a dried sample container, then sealed and heated to 110° C. under continuous stirring for 7 hours. After the reaction was completed, the mixture was cooled to room temperature to produce Precursor 5 having the following structure with a yield of about 99%. Precursor 5 was characterized by FT-IR spectroscopy and the result is shown in FIG. 5. According to FIG. 5, Precursor 5 has a characteristic absorption peak (C=O or C=N) at 1730 $cm^{-1}$, and the absorption peaks observed at 2270 $cm^{-1}$ and 2127 $cm^{-1}$ are assigned to remaining unreacted isocyanate and carbodiimide residue respectively.

[Precursor 5]

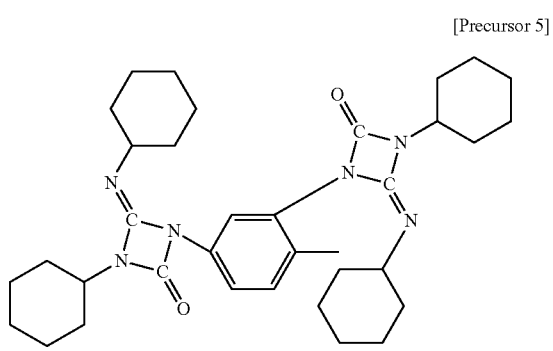 [SMILES: Cc1ccc(N2C(=O)N(C3CCCCC3)/C2=N/C2CCCCC2)cc1N1C(=O)N(C2CCCCC2)/C1=N/C1CCCCC1]

Example 6

Figure 6:
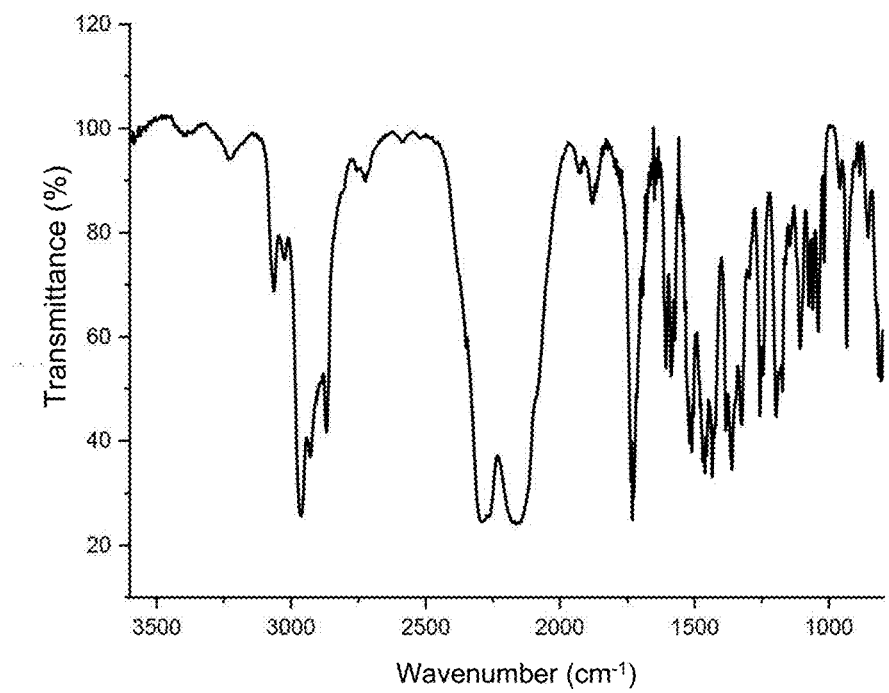

73.2 g of Stabaxol 1 was mixed with 25.6 g of methylene diphenyl diisocyanate (MDI). The mixture was placed in a dried sample container, then sealed and heated to 110° C. under continuous stirring for 7 hours. After the reaction was completed, the mixture was cooled to room temperature to produce Precursor 6 having the following structure with a yield of about 99%. Precursor 6 was characterized by FT-IR spectroscopy and the result is shown in FIG. 6. According to FIG. 6, Precursor 6 has a characteristic absorption peak (C=O or C=N) at 1720 $cm^{-1}$, and the absorption peaks observed at 2270 $cm^{-1}$ and 2154 $cm^{-1}$ are assigned to remaining unreacted isocyanate and carbodiimide residue respectively.

[Precursor 6]

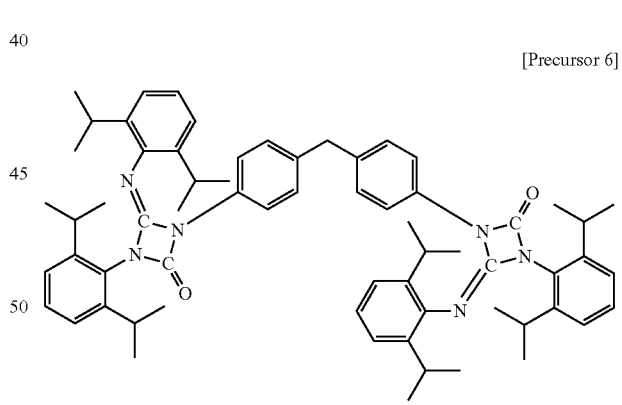

Example 7

Figure 7:
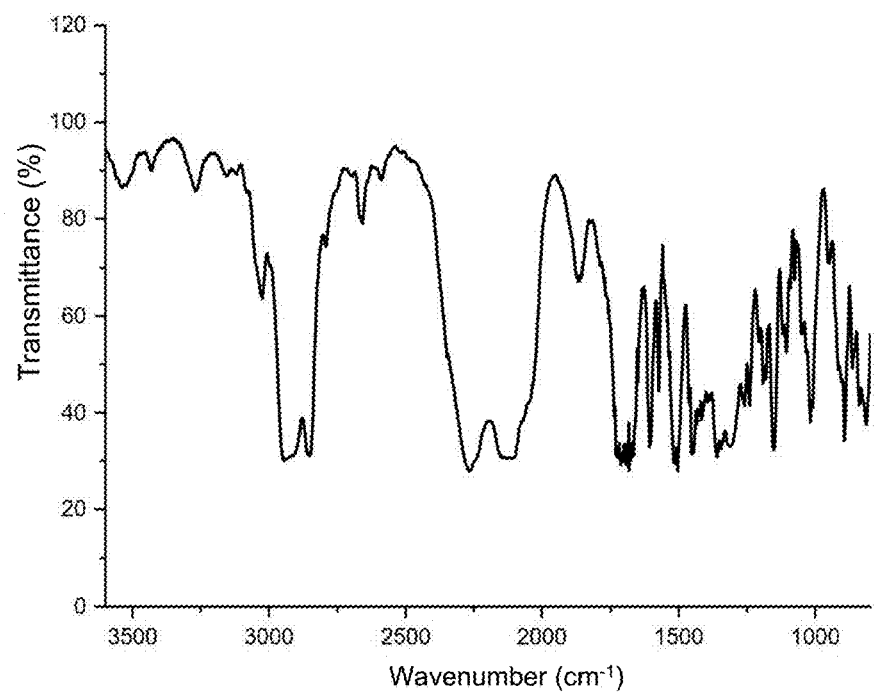

41.7 g of DCC was mixed with 25.6 g of MDI. The mixture was placed in a dried sample container, then sealed and heated to 110° C. under continuous stirring for 7 hours. After the reaction was completed, the mixture was cooled to room temperature to produce Precursor 7 having the following structure with a yield of about 97%. Precursor 7 was characterized by FT-IR spectroscopy and the result is shown in FIG. 7. According to FIG. 7, Precursor 7 has a characteristic absorption peak (C=O or C=N) at 1722 cm$^{-1}$, and the absorption peaks observed at 2270 cm$^{-1}$ and 2154 cm$^{-1}$ are assigned to remaining unreacted isocyanate and carbodiimide residue respectively.

[Precursor 7]

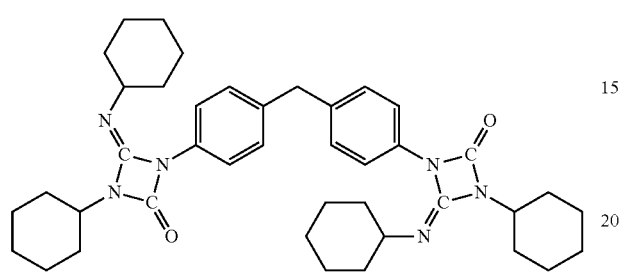

Example 8

Figure 8:
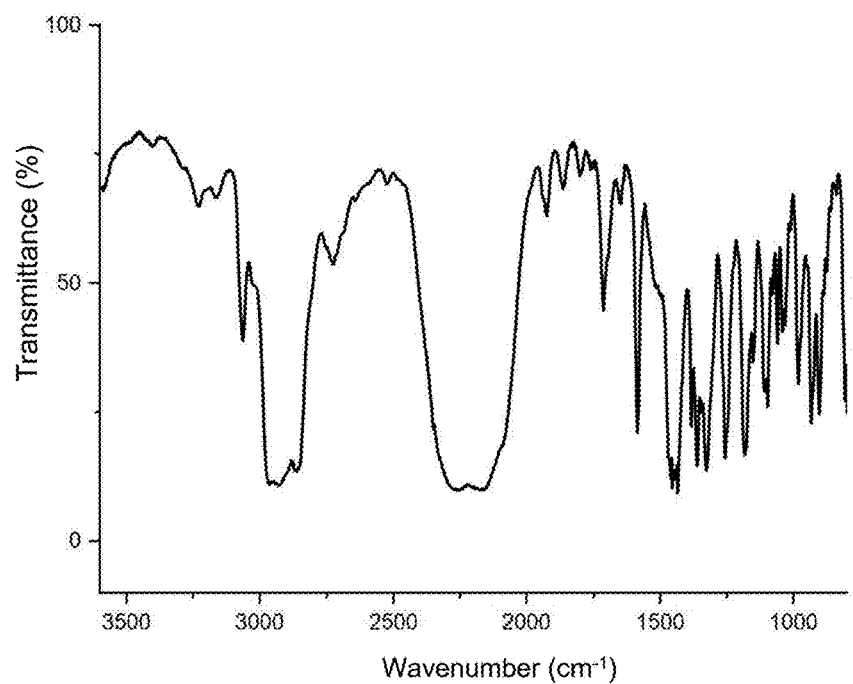

73.2 g of Stabaxol 1 was mixed with 26.5 g of 4,4'-dicyclohexylmethane diisocyanate (H12MDI). The mixture was placed in a dried sample container, then sealed and heated to 110° C. under continuous stirring for 7 hours. After the reaction was completed, the mixture was cooled to room temperature to produce Precursor 8 having the following structure with a yield of about 96%. Precursor 8 was characterized by FT-IR spectroscopy and the result is shown in FIG. 8. According to FIG. 8, Precursor 8 has a characteristic absorption peak at 1715 cm$^{-1}$, and the absorption peaks observed at 2270 cm$^{-1}$ and 2154 cm$^{-1}$ are assigned to remaining unreacted isocyanate and carbodiimide residue respectively.

[Precursor 8]

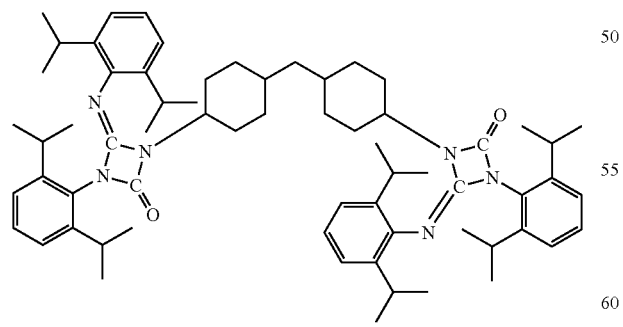

Example 9

Figure 9:
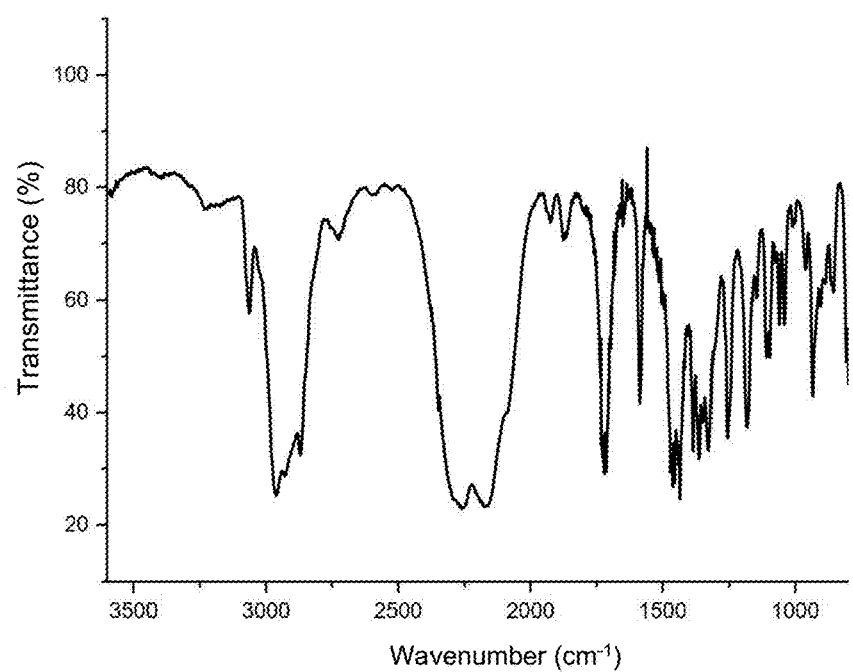

73.2 g of Stabaxol 1 was mixed with 22.3 g of isophorone diisocyanate (IPDI). The mixture was placed in a dried sample container, then sealed and heated to 110° C. under continuous stirring for 7 hours. After the reaction was completed, the mixture was cooled to room temperature to produce Precursor 9 having the following structure with a yield of about 98%. Precursor 9 was characterized by FT-IR spectroscopy and the result is shown in FIG. 9. According to FIG. 9, Precursor 9 has a characteristic absorption peak (C=O or C=N) at 1720 cm$^{-1}$, and the absorption peaks observed at 2270 cm$^{-1}$ and 2154 cm$^{-1}$ are assigned to remaining unreacted isocyanate and carbodiimide residue respectively.

[Precursor 9]

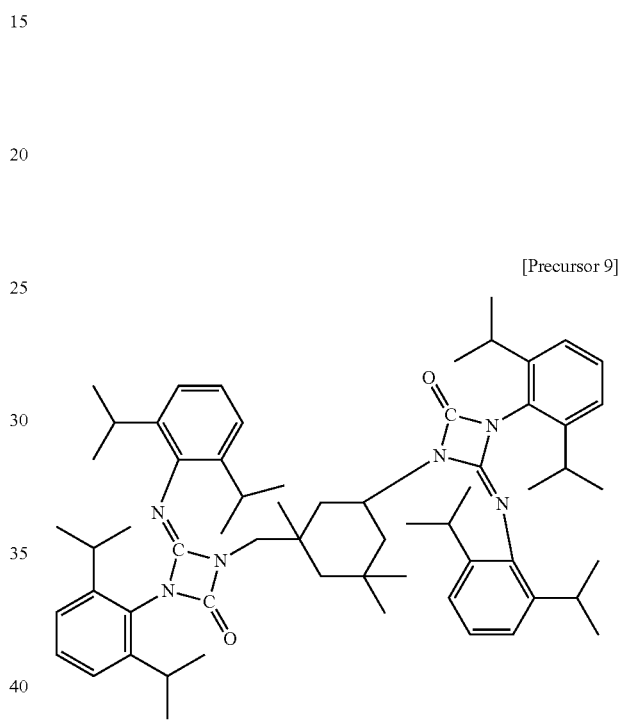

Example 10

Figure 10:
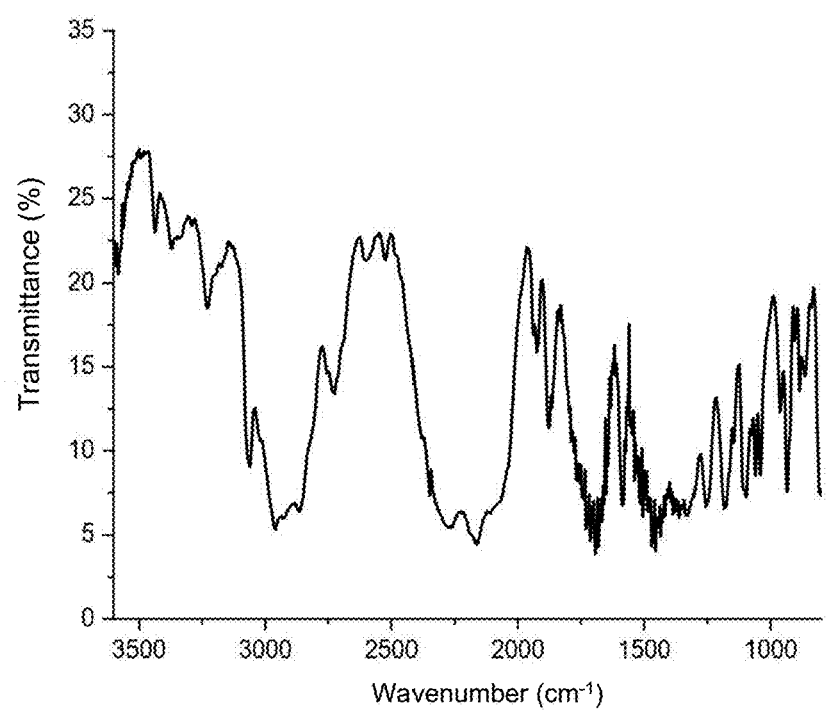

110 g of Stabaxol 1 was mixed with 50.5 g of hexamethylene diisocyanate trimer (HDI trimer). The mixture was placed in a dried sample container, then sealed and heated to 110° C. under continuous stirring for 7 hours. After the reaction was completed, the mixture was cooled to room temperature to produce Precursor 10 with a yield of about 98%. Precursor 10 was characterized by FT-IR spectroscopy and the result is shown in FIG. 10. According to FIG. 10, Precursor 10 has a characteristic absorption peak (C=O or C=N) at 1716 cm$^{-1}$, and the absorption peaks observed at 2270 cm$^{-1}$ and 2154 cm$^{-1}$ are assigned to remaining unreacted isocyanate and carbodiimide residue respectively.

[Precursor 10]

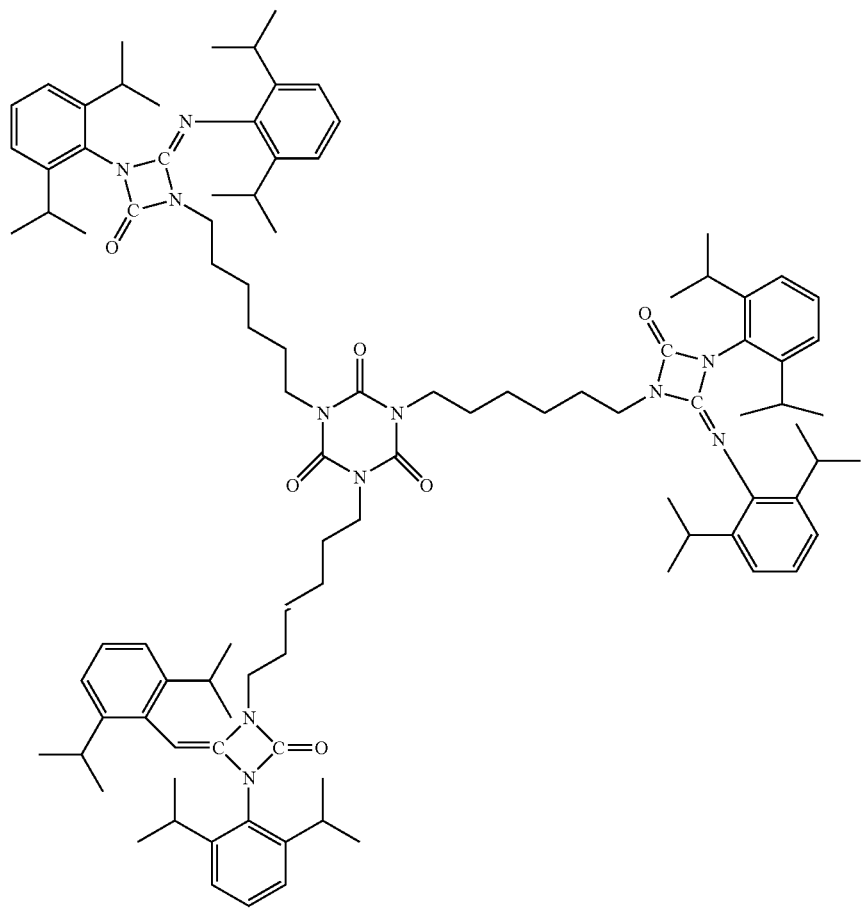

Example 11

Figure 11:
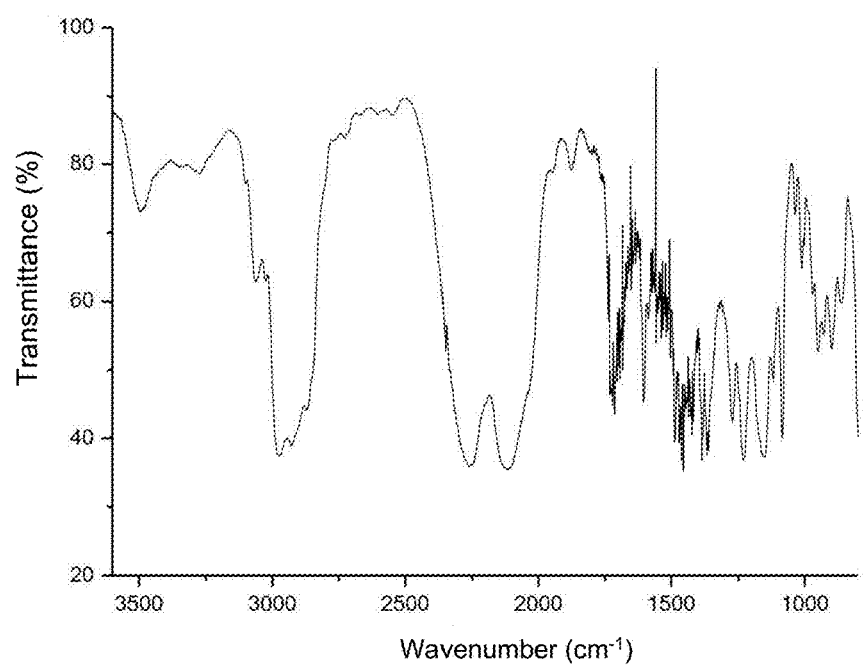

52.6 g of a carbodiimide oligomer (CARBODILITE V-05, purchased from Nisshinbo Chemical Inc.) was mixed with 22.3 g of IPDI. The mixture was placed in a dried sample container, then sealed and heated to 110° C. under continuous stirring for 7 hours. After the reaction was completed, the mixture was cooled to room temperature to produce Precursor 11 with a yield of about 99%. Precursor 11 was characterized by FT-IR spectroscopy and the result is shown in FIG. 11. According to FIG. 11, Precursor 11 has a characteristic absorption peak (C=O or C=N) at 1728 cm$^{-1}$, and the absorption peaks observed at 2265 cm$^{-1}$ and 2132 cm$^{-1}$ are assigned to remaining unreacted isocyanate and carbodiimide residue respectively.

[Preparation of Flame Retardants]

Example 12

Figure 12:
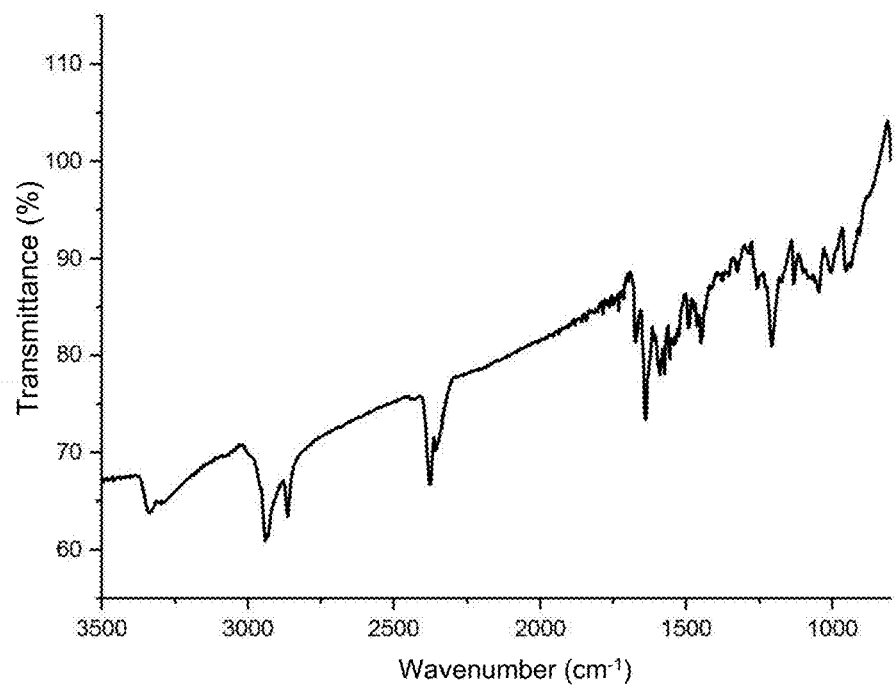
FIG. 12 is an FT-IR spectrum of flame retardant 1 obtained in Example 12 of the present disclosure.
Figure 13A:
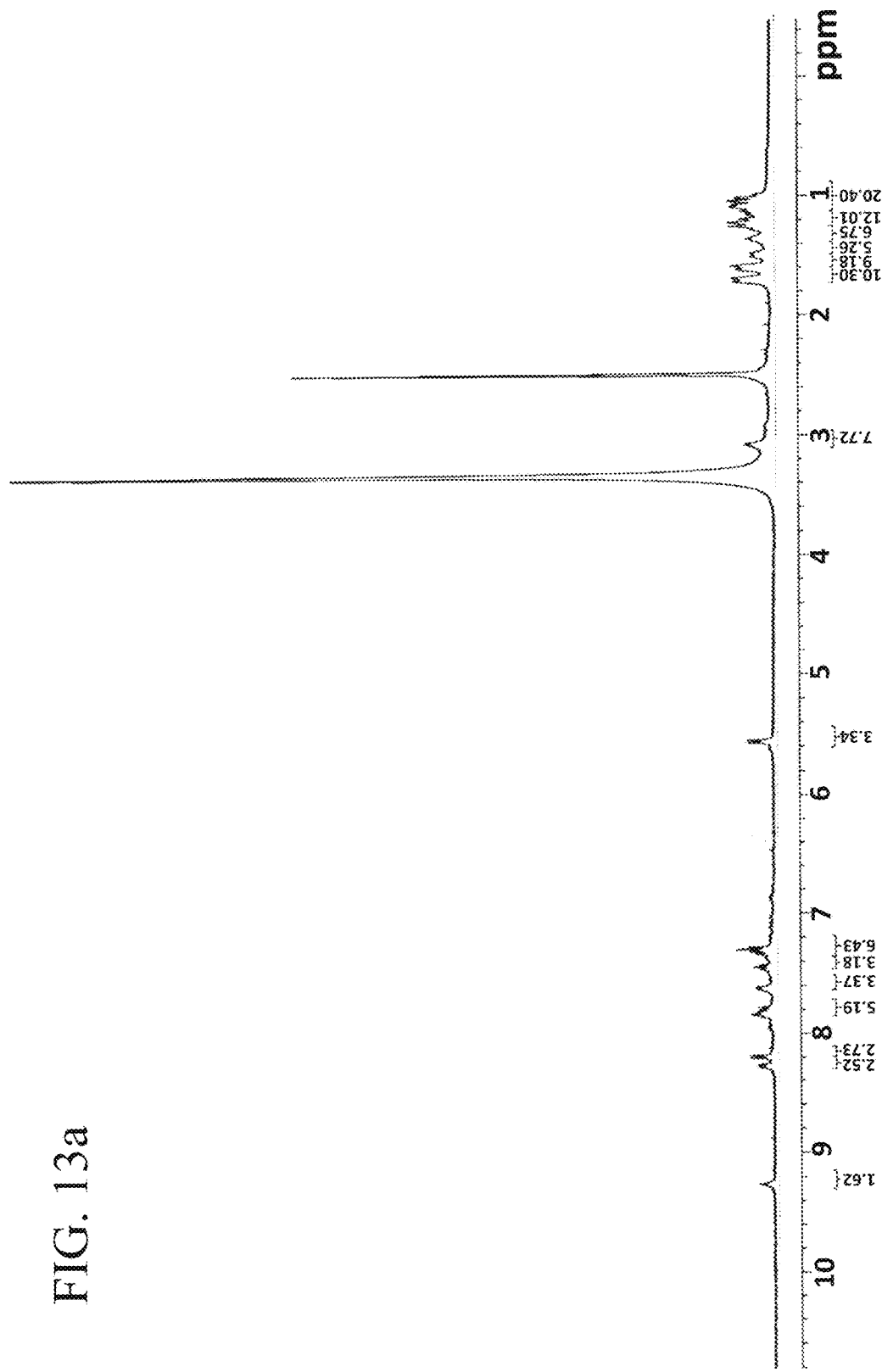
FIGS. 13*a* and 13*b* are $^1$H NMR spectra of the flame retardant 1 obtained in Example 12 of the present disclosure.
Figure 13B:
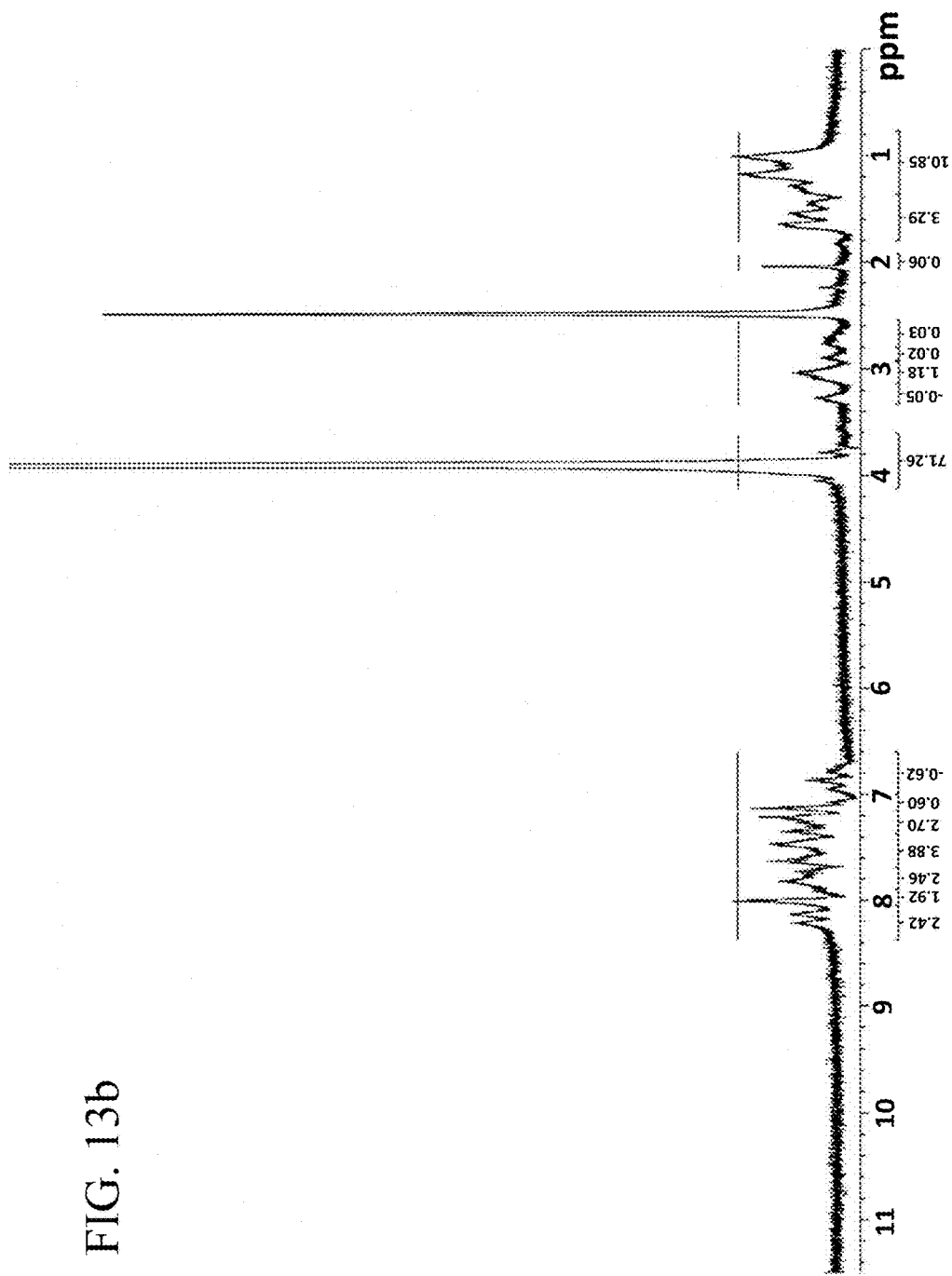

58 g of Precursor 3 and an excess amount of 9, 10-dihydro-9-oxa-10-phosphaphenanthrene-10-oxide (DOPO, 157 g) were mixed and placed in a 500 mL three-neck flask. Then, 300 mL of toluene was added to the flask and heated to 130° C. under continuous stirring for 60 hours. After the reaction was completed, the mixture was cooled to room temperature. The precipitate was filtered and dried under suction to produce Flame Retardant 1 having the following structure with a yield of about 90%. Flame Retardant 1 was characterized by FT-IR and $^1$H NMR spectroscopy and the results are shown in FIG. 12 and FIGS. 13a and 13b respectively.

[Flame Retardant 1]

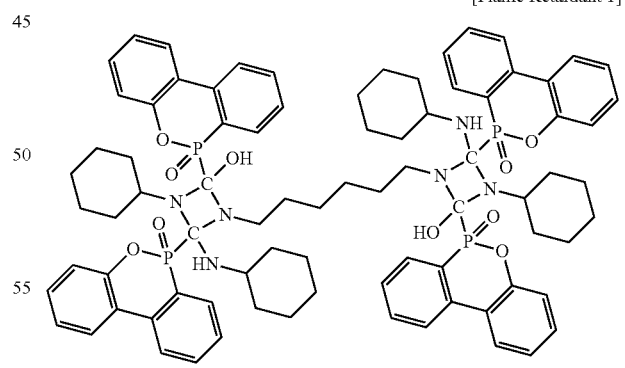

In comparison with the spectrum of Flame Retardant 1 (FIG. 12) and the spectrum of Precursor 3 (FIG. 3), it is obviously that the characteristic absorption peak at 1722 cm$^{-1}$ of Precursor 3 in FIG. 3 is disappeared. In addition, according to the $^1$H NMR spectrum of Flame Retardant 1 shown in FIG. 13a, the result of the $^1$H NMR recorded at 600 MHz in DMSO-d$_6$ is: δ 7.2-8.3 (Ar—H), δ 5.5 (d, 1H, N—H), δ 9.2 (s, 1H, O—H). After D$_2$O is added dropwise, as shown in FIG. 13b, the characteristic peaks of amino group (NH group) and hydroxyl group (OH group) are disappeared, confirming that Flame Retardant 1 contains both NH and OH groups which are reactive functional groups.

Example 13

Figure 14:
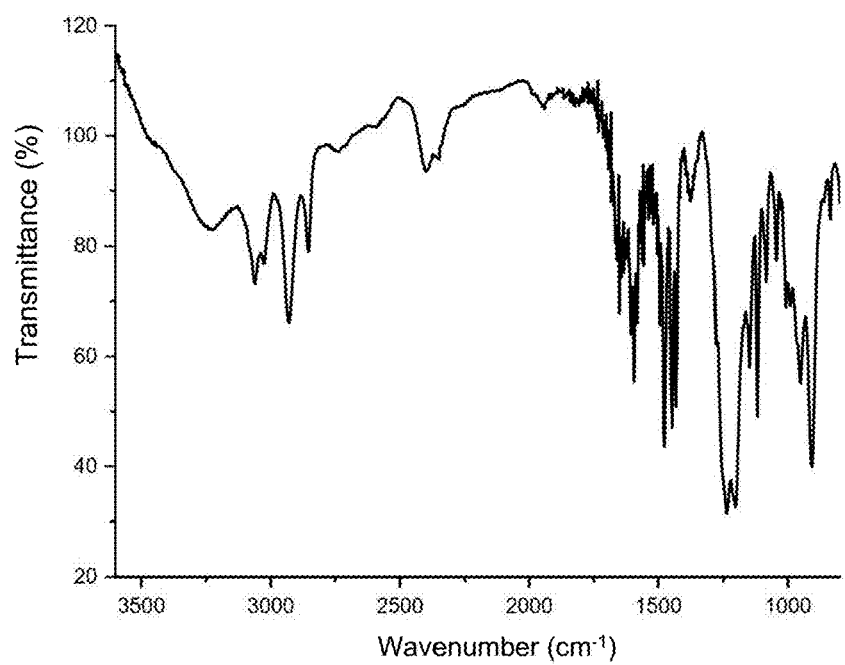
FIG. 14 is an FT-IR spectrum of flame retardant 2 obtained in Example 13 of the present disclosure.
Figure 15A:
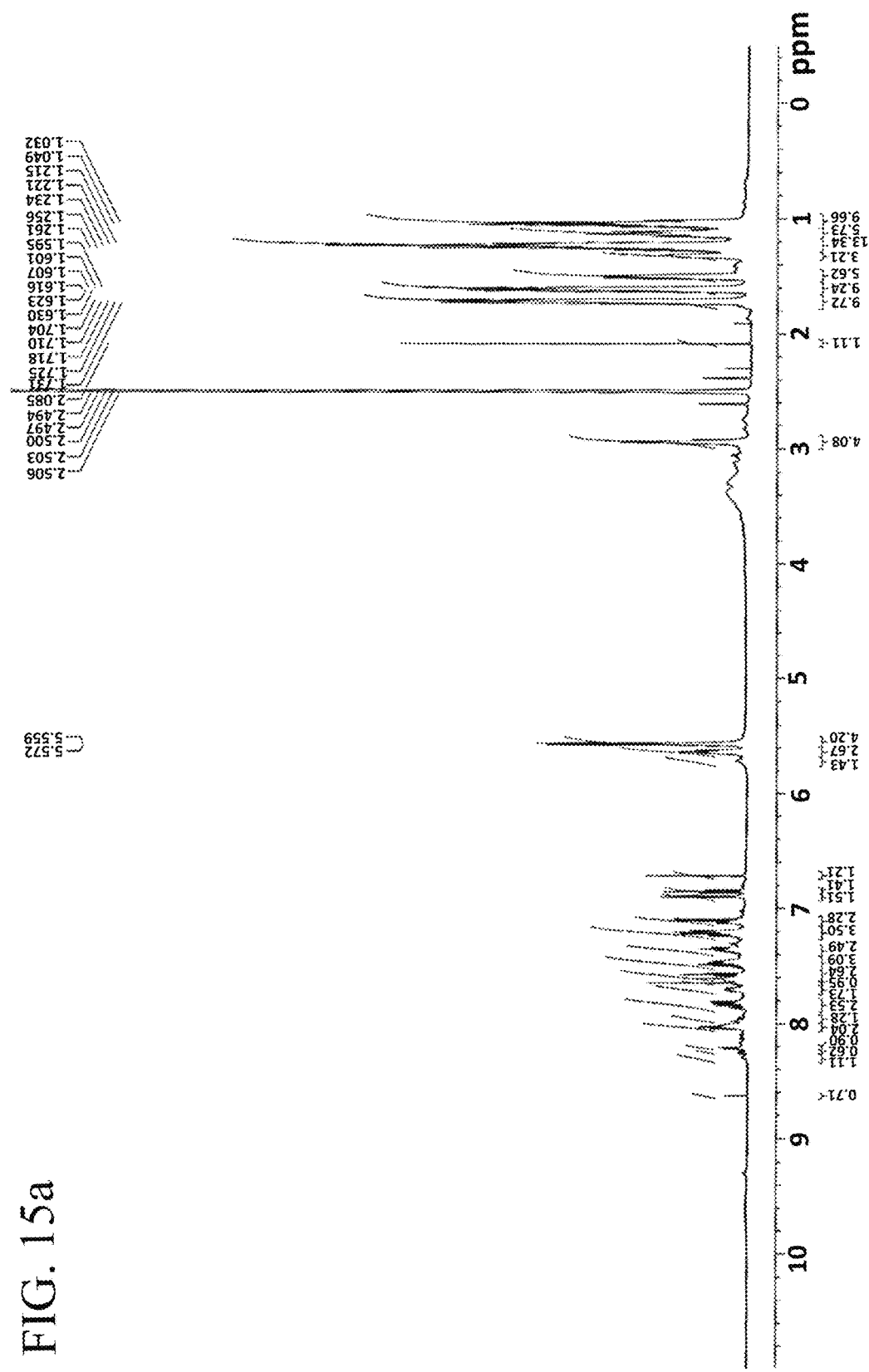
FIGS. 15*a* and 15*b* are $^1$H NMR spectra of the flame retardant 2 obtained in Example 13 of the present disclosure.
Figure 15B:
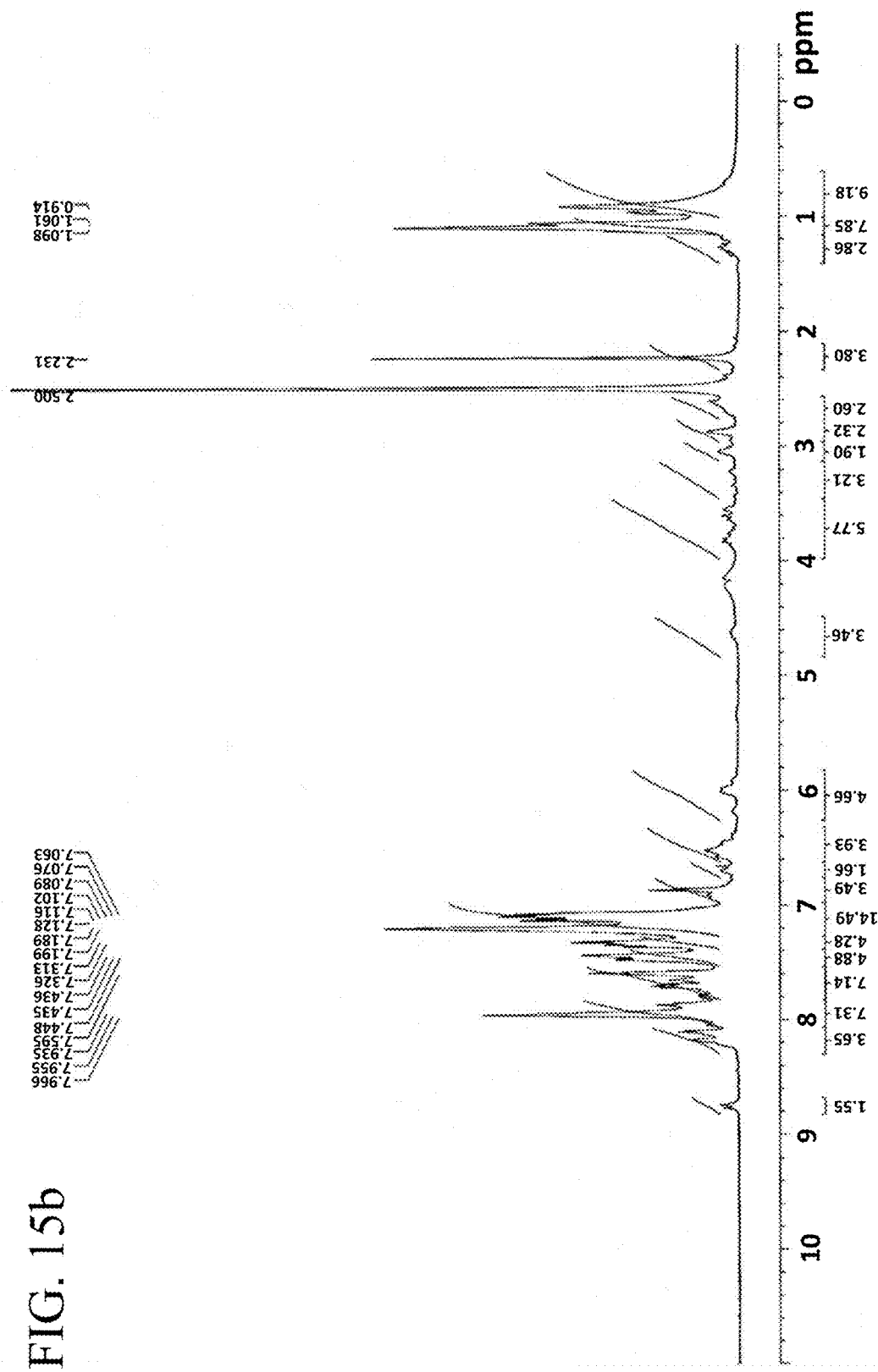

58 g of Precursor 3 and 92 g of DOPO were mixed and placed in a 500 mL three-neck flask. Then, 300 mL of toluene was added to the flask and heated to 80° C. under continuous stirring for 45 hours. After the reaction was completed, the mixture was cooled to room temperature. The precipitate was filtered and dried under suction to produce Flame Retardant 2 having the following structure with a yield of about 70%. Flame Retardant 2 was characterized by FT-IR and $^1$H NMR spectroscopy and the results are shown in FIG. 14 and FIGS. 15a and 15b respectively.

[Flame Retardant 2]

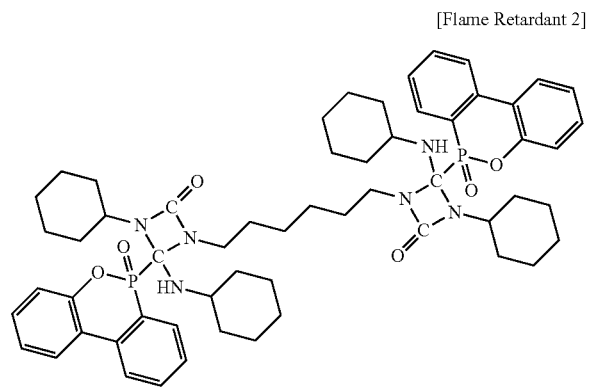 [SMILES: O=C1N(CCCCCCN2C(=O)N(C3CCCCC3)C2(NC2CCCCC2)P2(=O)Oc3ccccc3-c3ccccc32)C(NC2CCCCC2)(P2(=O)Oc3ccccc3-c3ccccc32)N1C1CCCCC1]

In comparison with the spectrum of Flame Retardant 2 (FIG. 14) and the spectrum of Precursor 3 (FIG. 3), it is obviously that the characteristic absorption peak at 1722 cm$^{-1}$ of Precursor 3 in FIG. 3 is disappeared. In addition, according to the $^1$H NMR spectrum of Flame Retardant 2 shown in FIG. 15a, the result of the $^1$H NMR recorded at 600 MHz in DMSO-$d_6$ is: δ 6.8 to 8.3 (Ar—H), δ 5.5 (d, 1H, N—H). After D$_2$O is added dropwise, as shown in FIG. 15b, the characteristic peak of NH group is disappeared, confirming that Flame Retardant 2 contains NH group which is reactive functional group.

Example 14

Figure 16:
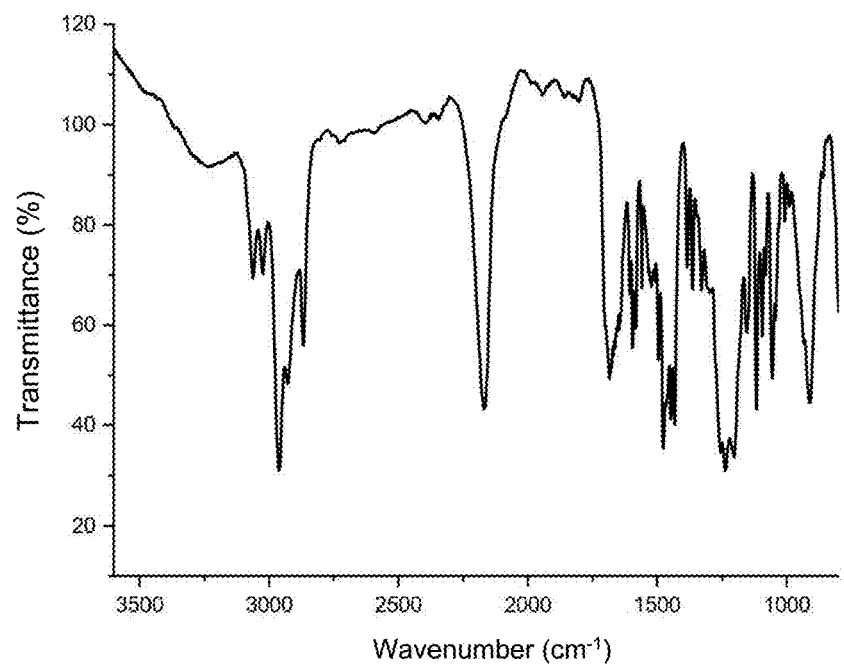
FIG. 16 is an FT-IR spectrum of flame retardant 3 obtained in Example 14 of the present disclosure.
Figure 17A:
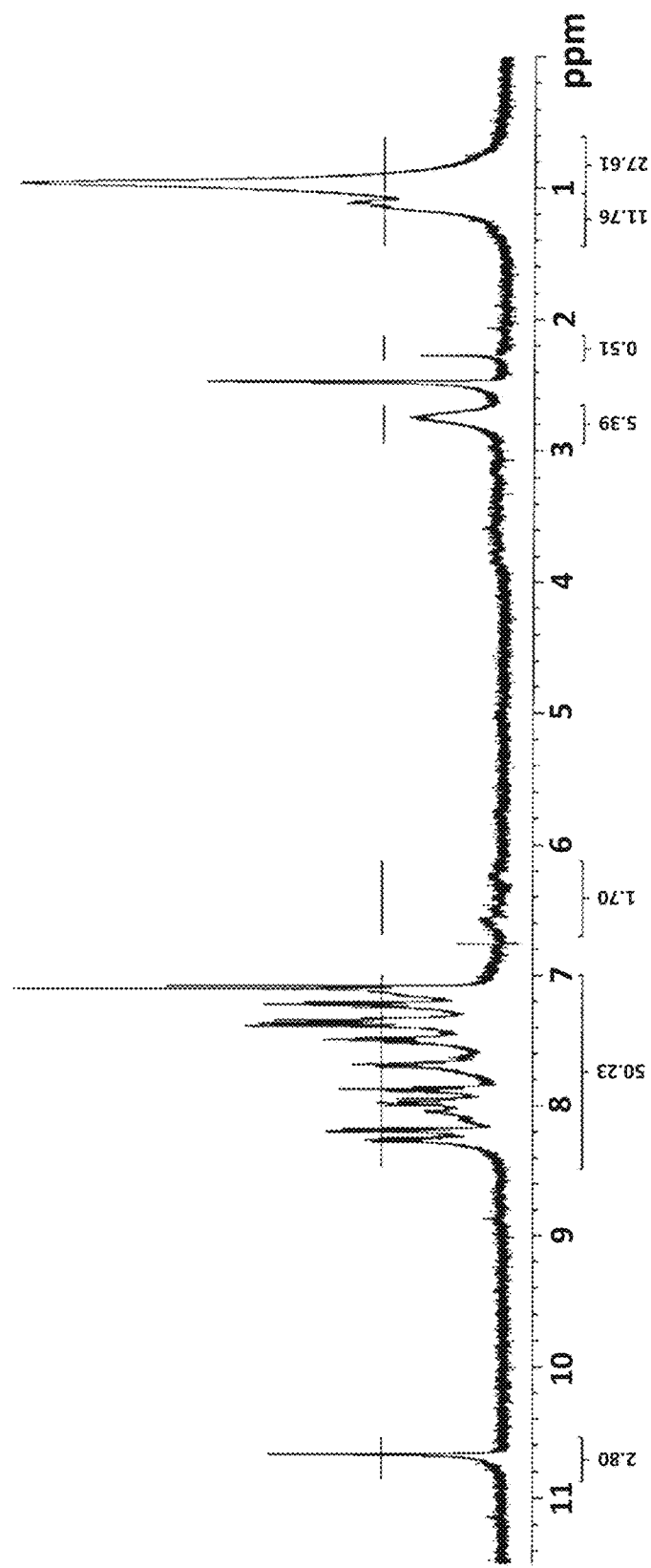
FIGS. 17*a* and 17*b* are $^1$H NMR spectra of the flame retardant 3 obtained in Example 14 of the present disclosure.
Figure 17B:
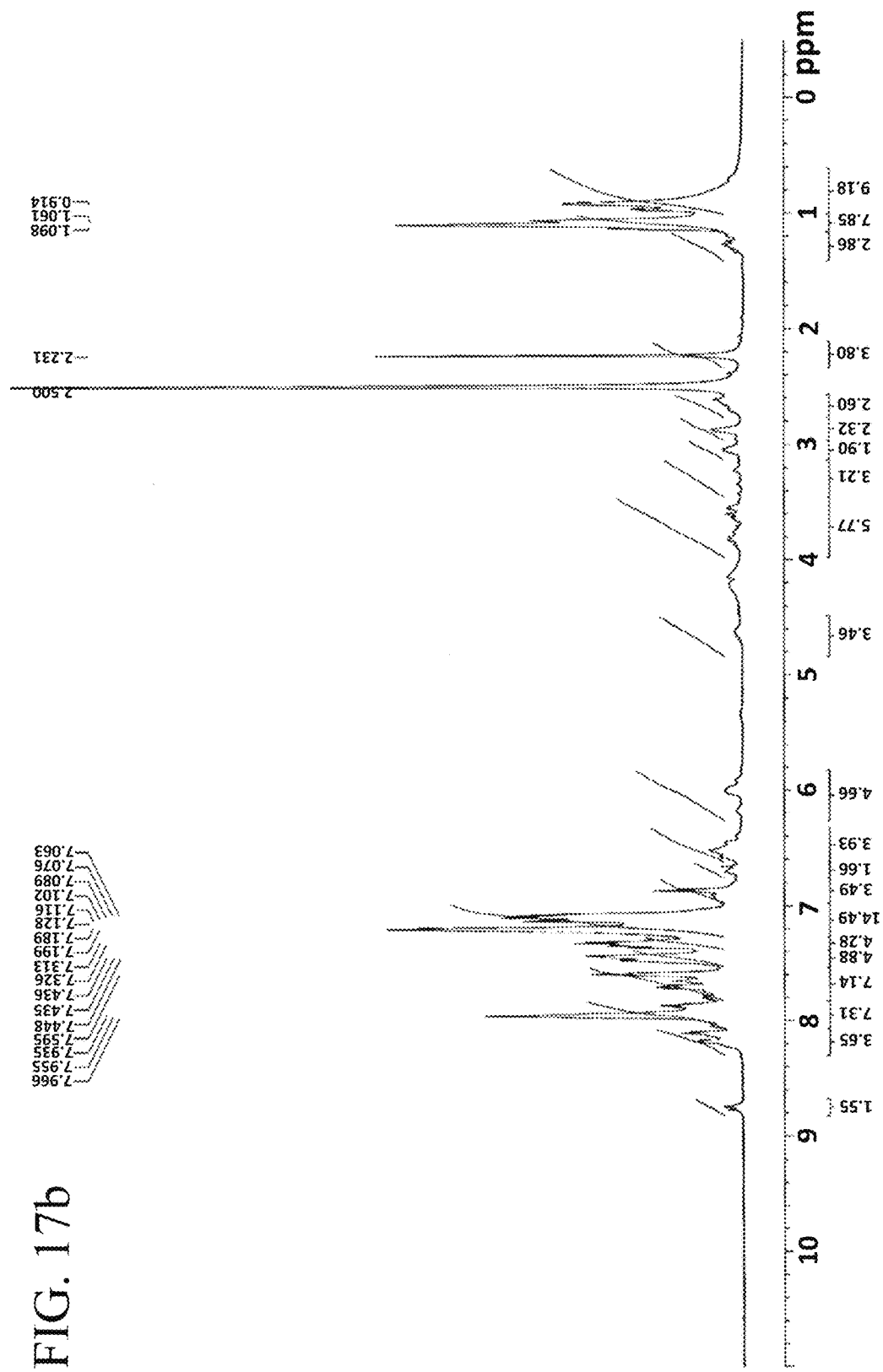

88 g of Precursor 4 and an excess amount of DOPO (95 g) were mixed and placed in a 500 mL three-neck flask. Then, 300 mL of toluene was added to the flask and heated to 80° C. under continuous stirring for 60 hours. After the reaction was completed, the mixture was cooled to room temperature. The precipitate was filtered and dried under suction to produce Flame Retardant 3 having the following structure with a yield of about 71%. Flame Retardant 3 was characterized by FT-IR and $^1$H NMR spectroscopy and the results are shown in FIG. 16 and FIGS. 17a and 17b respectively.

[Flame Retardant 3]

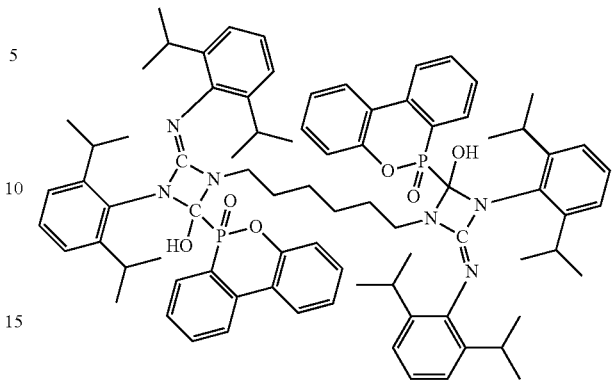

In comparison with the spectrum of Flame Retardant 3 (FIG. 16) and the spectrum of Precursor 4 (FIG. 4), it is obviously that the characteristic absorption peak at 1728 cm$^{-1}$ of Precursor 4 in FIG. 4 is disappeared. In addition, according to the $^1$H NMR spectrum of Flame Retardant 3 shown in FIG. 17a, the result of the $^1$H NMR recorded at 600 MHz in DMSO-$d_6$ is: δ 7.0 to 8.4 (Ar—H), δ 10.7 (s, 1H, O—H). After D$_2$O is added dropwise, as shown in FIG. 17b, the characteristic peak of OH group is disappeared, confirming that Flame Retardant 3 contains OH group which is reactive functional group.

Example 15

Figure 18:
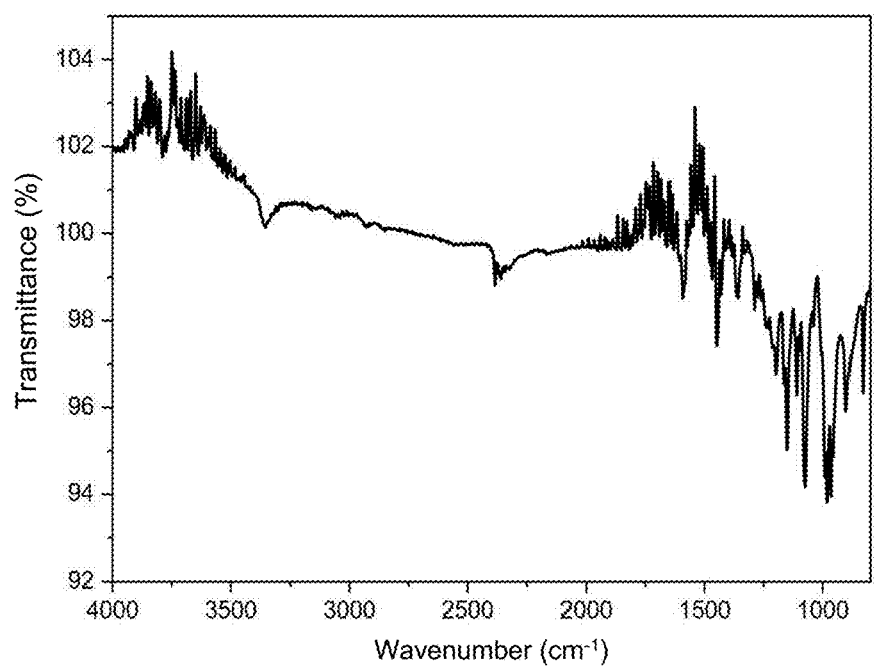
FIG. 18 is an FT-IR spectrum of flame retardant 4 obtained in Example 15 of the present disclosure.

59 g of Precursor 5 and an excess amount of DOPO (115 g) were mixed and placed in a 1000 mL three-neck flask. Then, 400 mL of toluene was added to the flask and heated to 75° C. under continuous stirring for 60 hours. After the reaction was completed, the mixture was cooled to room temperature. The precipitate was filtered and dried under suction to produce Flame Retardant 4 having the following structure with a yield of about 77%. Flame Retardant 4 was characterized by FT-IR and $^1$H NMR spectroscopy and the spectrum is shown in FIG. 18.

[Flame Retardant 4]

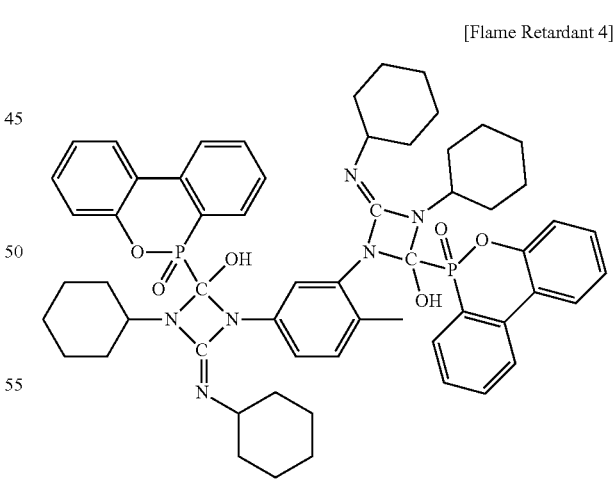

In comparison with the spectrum of Flame Retardant 4 (FIG. 18) and the spectrum of Precursor 5 (FIG. 5), it is obviously that the characteristic absorption peak at 1730 cm$^{-1}$ of Precursor 5 in FIG. 5 is disappeared. In addition, the result of the $^1$H NMR of Flame Retardant 4 recorded at 600 MHz in DMSO-$d_6$ is: δ 6.7 to 8.4 (Ar—H), δ 8.9 (s, 1H, O—H), confirming that Flame Retardant 4 contains OH group which is reactive functional group.

Example 16

Figure 19:
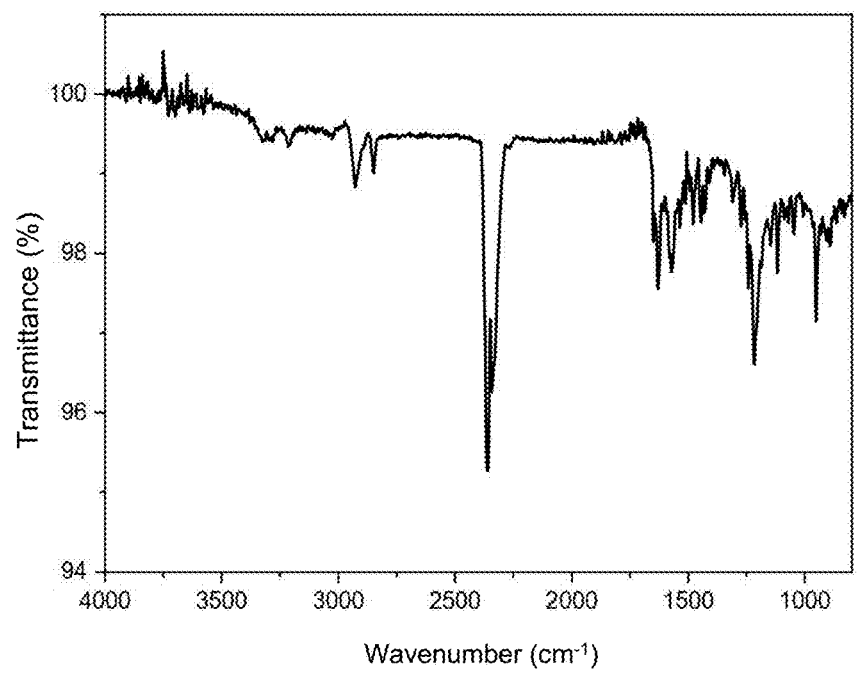
FIG. 19 is an FT-IR spectrum of flame retardant 5 obtained in Example 16 of the present disclosure.

63 g of Precursor 7 and an excess amount of DOPO (160 g) were mixed and placed in a 500 mL three-neck flask. Then, 350 mL of toluene was added to the flask and heated to 130° C. under continuous stirring for 60 hours. After the reaction was completed, the mixture was cooled to room temperature. The precipitate was filtered and dried under suction to produce Flame Retardant 5 having the following structure with a yield of about 73%. Flame Retardant 5 was characterized by FT-IR and $^1$H NMR spectroscopy and the spectrum is shown in FIG. 19.

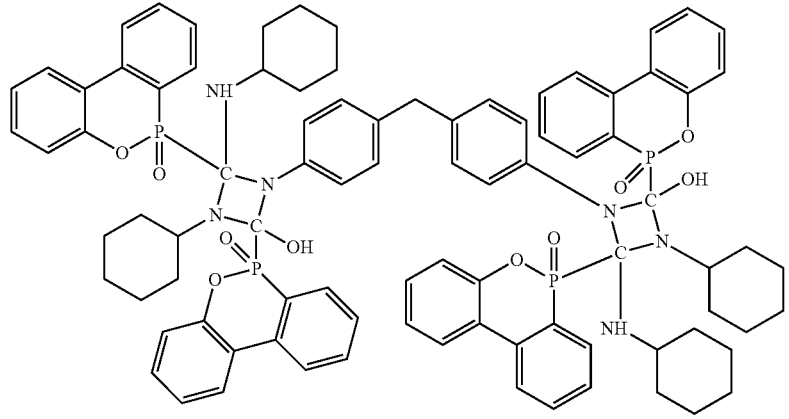

[Flame Retardant 5]

In comparison with the spectrum of Flame Retardant 5 (FIG. 19) and the spectrum of Precursor 7 (FIG. 7), it is obviously that the characteristic absorption peak at 1722 cm$^{-1}$ of Precursor 7 in FIG. 7 is disappeared. In addition, the result of the $^1$H NMR of Flame Retardant 5 recorded at 600 MHz in DMSO-d$_6$ is: δ 6.9-8.3 (Ar—H), δ 5.5-5.9 (d, 1H, N—H), δ 8.9 (s, 1H, O—H), confirming that Flame Retardant 5 contains both NH and OH groups which are reactive functional groups.

Example 17

Figure 20:
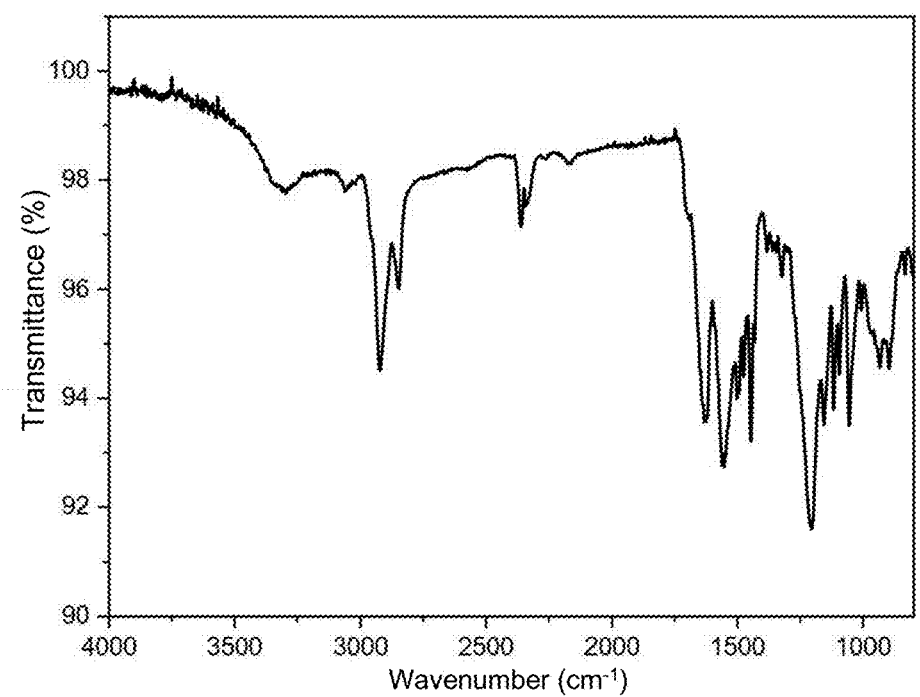
FIG. 20 is an FT-IR spectrum of flame retardant 6 obtained in Example 17 of the present disclosure.

99 g of Precursor 8 and 110 g of DOPO are mixed and placed in a 500 mL three-neck flask. Then, 300 mL of toluene was added to the flask and heated to 80° C. under continuous stirring for 45 hours. After the reaction was completed, the mixture was cooled to room temperature. The precipitate was filtered and dried under suction to produce Flame Retardant 6 having the following structure with a yield of about 72%. Flame Retardant 6 was characterized by FT-IR and $^1$H NMR spectroscopy and the spectrum is shown in FIG. 20.

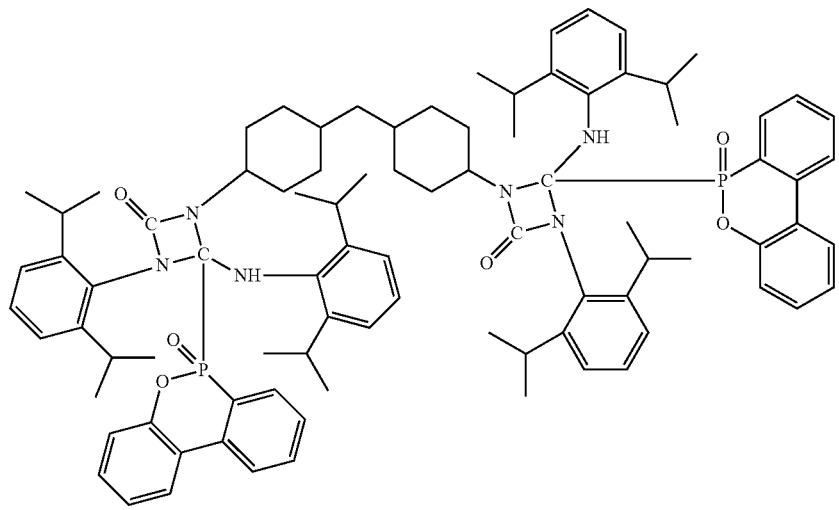

[Flame Retardant 6]

In comparison with the spectrum of Flame Retardant 6 (FIG. 20) and the spectrum of Precursor 8 (FIG. 8), it is obviously that the characteristic absorption peak at 1715 cm$^{-1}$ of Precursor 8 in FIG. 8 is disappeared. In addition, the result of the $^1$H NMR of Flame Retardant 6 recorded at 600 MHz in DMSO-d$_6$ is: δ 7.2-8.3 (Ar—H), δ 5.5 (d, 1H, N—H), confirming that Flame Retardant 6 contains NH group which is reactive functional group.

Example 18

Figure 21:
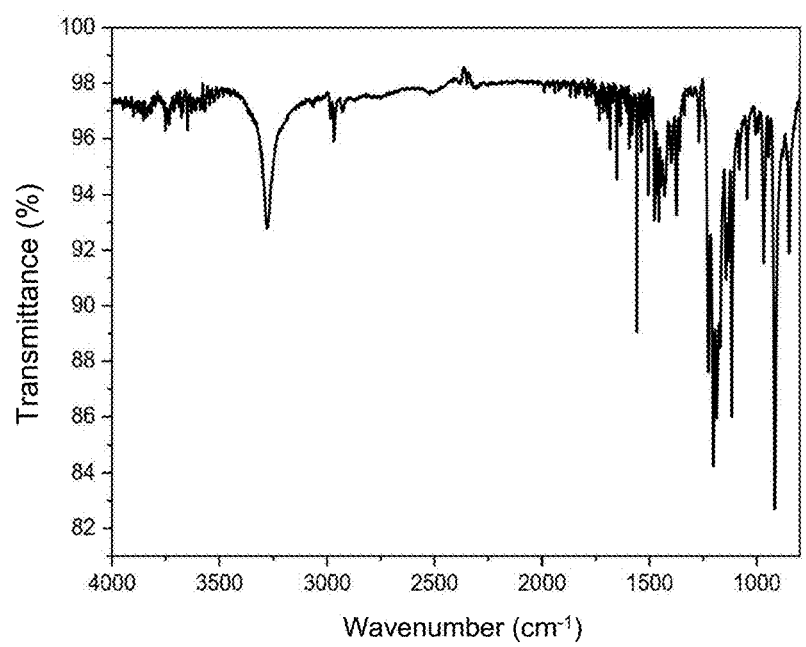
FIG. 21 is an FT-IR spectrum of flame retardant 7 obtained in Example 18 of the present disclosure.
Figure 22A:
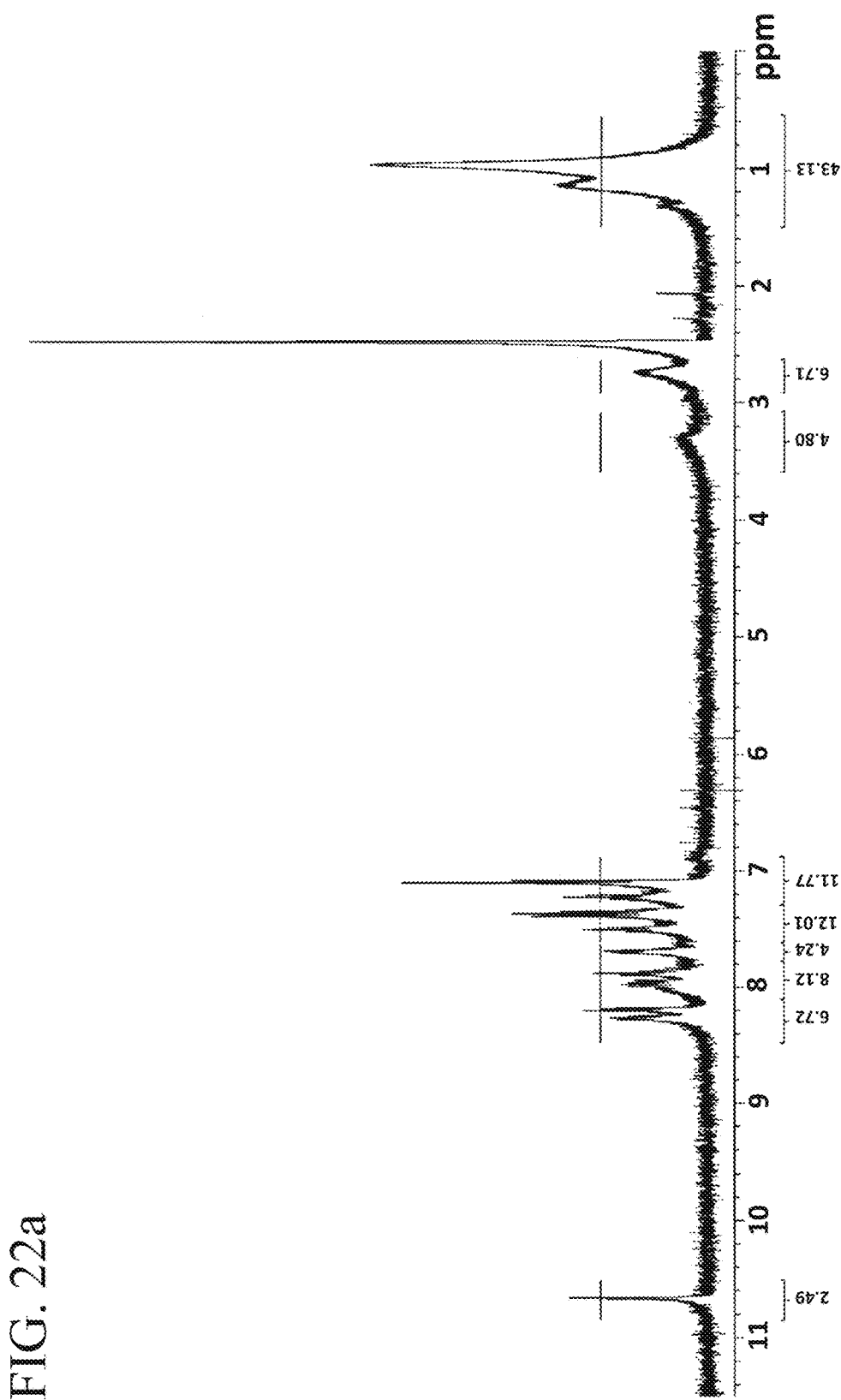
FIGS. 22a and 22b are $^1$H NMR spectra of the flame retardant 7 obtained in Example 18 of the present disclosure.
Figure 22B:
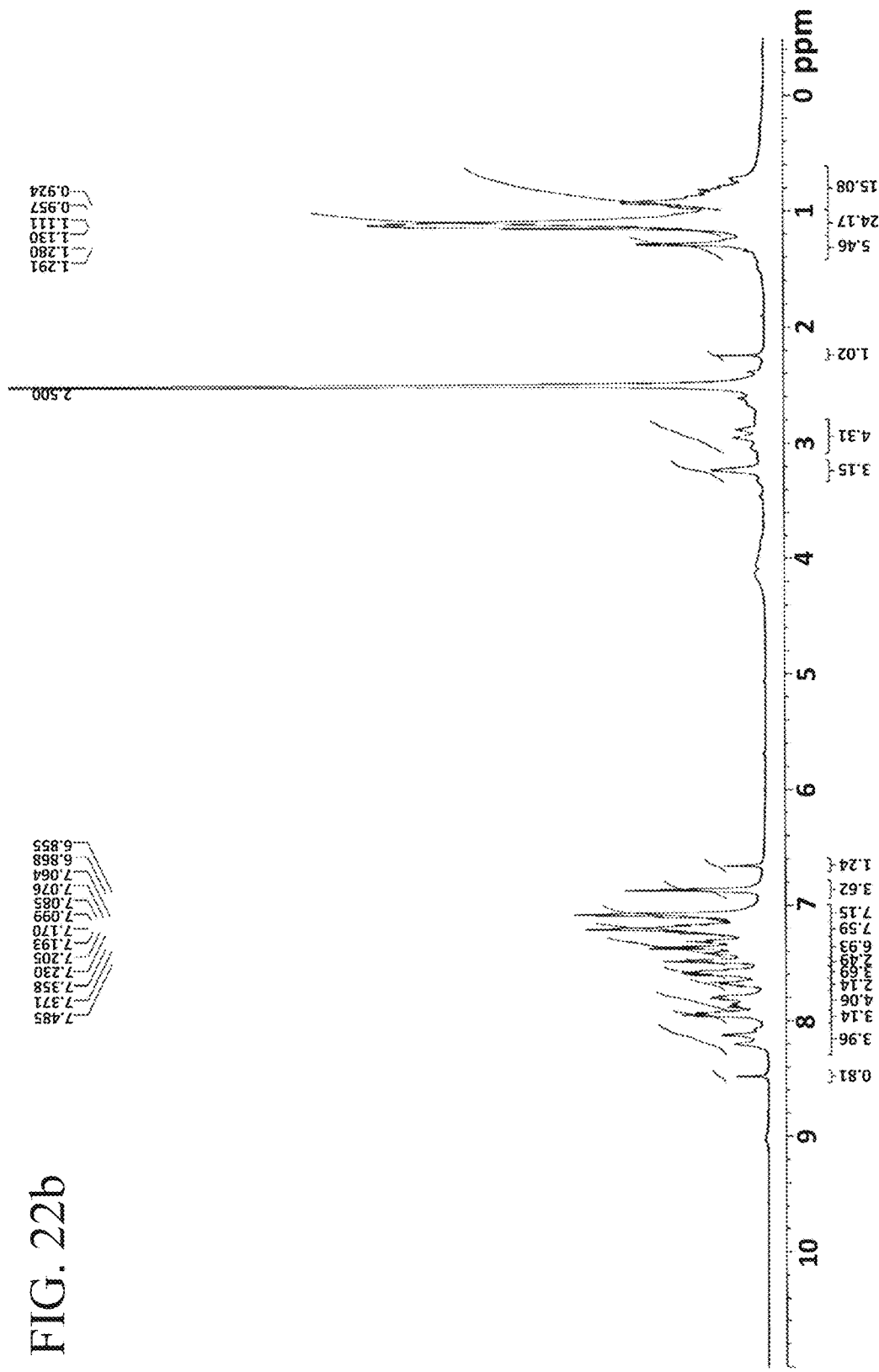

94 g of Precursor 9 and an excess amount of DOPO (115 g) are mixed and placed in a 1000 mL three-neck flask. Then, 400 mL of toluene was added to the flask and heated to 75° C. under continuous stirring for 60 hours. After the reaction was completed, the mixture was cooled to room temperature. The precipitate was filtered and dried under suction to produce Flame Retardant 7 having the following structure with a yield of about 68%. Flame Retardant 7 was characterized by FT-IR and $^1$H NMR spectroscopy and the results are shown in FIG. 21 and FIGS. 22a and 22b respectively.

[Flame Retardant 7]

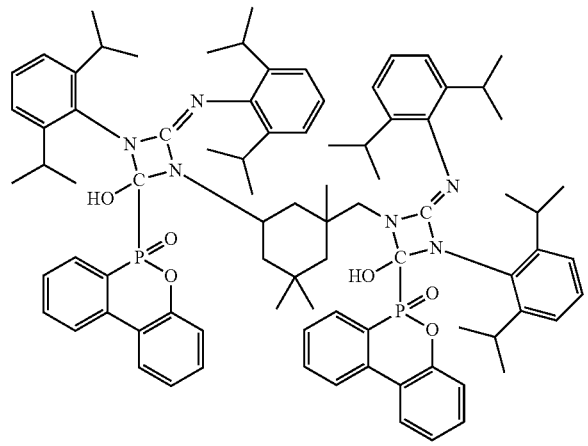

In comparison with the spectrum of Flame Retardant 7 (FIG. 21) and the spectrum of Precursor 9 (FIG. 9), it is obviously that the characteristic absorption peak at 1720 cm$^{-1}$ of Precursor 9 in FIG. 9 is disappeared. In addition, according to the $^1$H NMR spectrum of Flame Retardant 7 shown in FIG. 22a, the result of the $^1$H NMR recorded at 600 MHz in DMSO-d$_6$ is: δ 7.1 to 8.4 (Ar—H), δ 10.7 (s, 1H, O—H). After D$_2$O is added dropwise, as shown in FIG. 22b, the characteristic peak of OH group is disappeared, confirming that Flame Retardant 7 contains OH group which is reactive functional group.

Example 19

Figure 24:
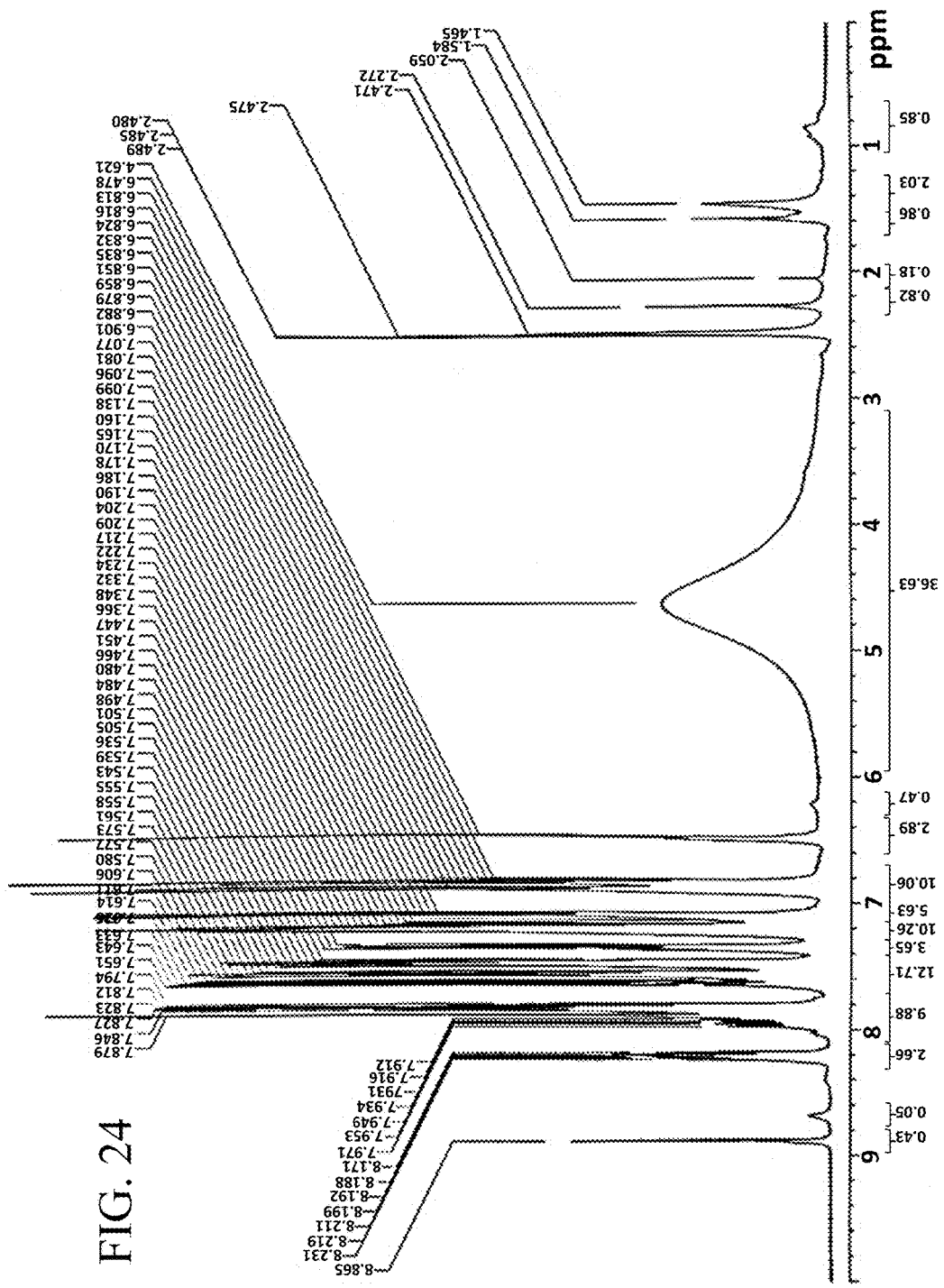
FIG. 24 is a $^1$H NMR spectrum of the flame retardant 8 obtained in Example 19 of the present disclosure.
Figure 23:
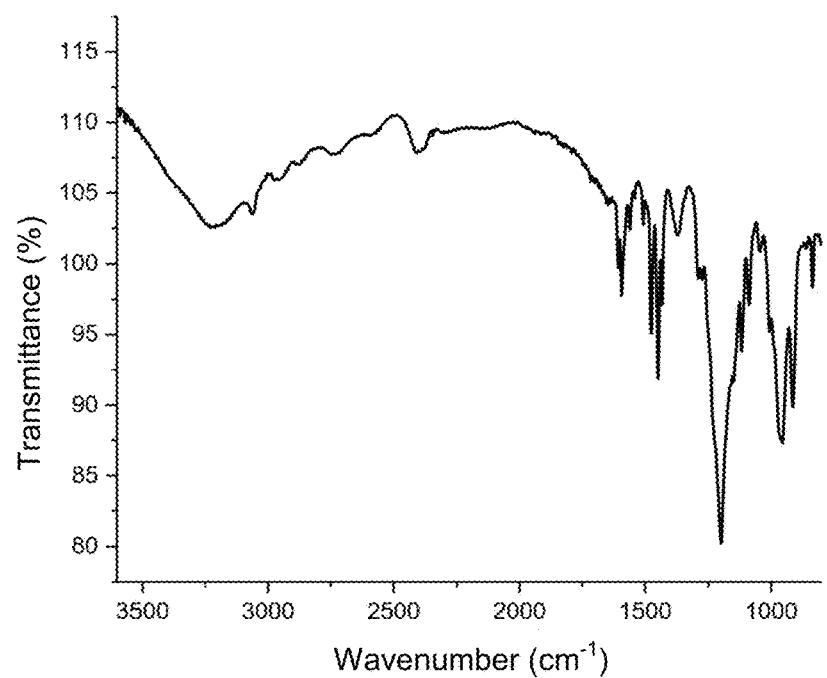
FIG. 23 is an FT-IR spectrum of flame retardant 8 obtained in Example 19 of the present disclosure.

38 g of Precursor 11 and 100 g of DOPO were mixed and placed in a 1000 mL three-neck flask. Then, 450 mL of toluene was added to the flask and heated to 95° C. under continuous stirring for 48 hours. After the reaction was completed, the mixture was cooled to room temperature. The precipitate was filtered and dried under suction to produce Flame Retardant 8 with a yield of about 92%. Flame Retardant 8 was characterized by FT-IR and $^1$H NMR spectroscopy. The results are shown in FIG. 23 and FIG. 24 respectively.

In comparison with the spectrum of Flame Retardant 8 (FIG. 23) and the spectrum of Precursor 11 (FIG. 11), it is obviously that the characteristic absorption peak at 1728 cm$^{-1}$ of Precursor 11 in FIG. 11 is disappeared. In addition, according to the $^1$H NMR spectrum of Flame Retardant 8 shown in FIG. 24, the result of the $^1$H NMR recorded at 600 MHz in DMSO-d$_6$ is: δ 6.8-8.4 (Ar—H), δ 8.7 and 8.9 (s, 1H, O—H), confirming that Flame Retardant 8 contains OH group which is reactive functional group.

[Reactivity Test of Flame Retardants]

3 g of Flame Retardant 1 and an excess amount of glycidyl methacrylate (GMA, 12 g) having an epoxy group were mixed and placed in a 200 mL three-neck flask. Then 150 mL of acetone was added to the flask and heated to 65° C. under continuous stirring for 1 hour. The obtained product was characterized by FT-IR spectroscopy and the result is shown in FIG. 25.

Figure 25:
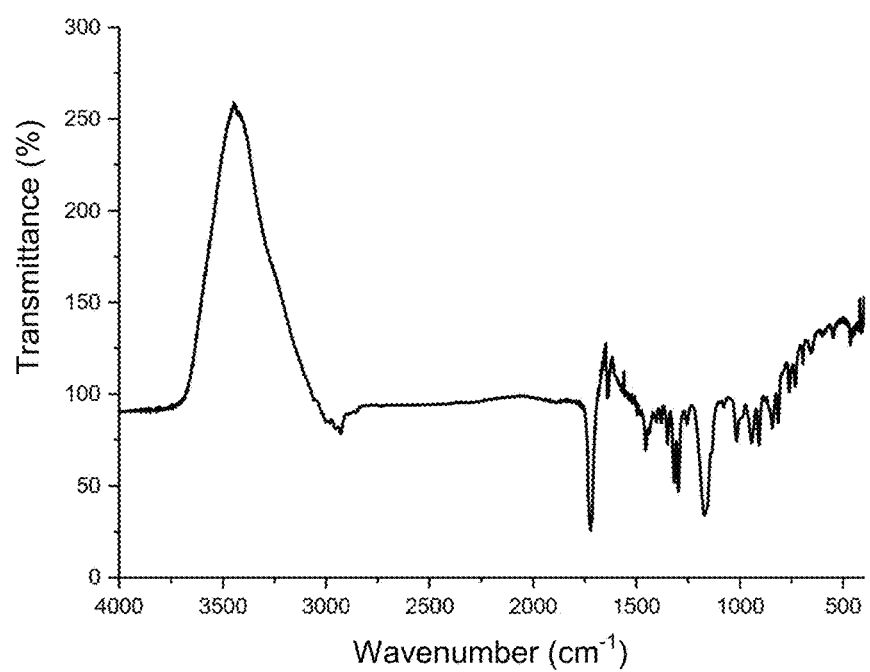
FIG. 25 is an FT-IR spectrum of a product in a reactivity test according to the present disclosure.

In comparison with the spectrum of Flame Retardant 1 (FIG. 12) and the spectrum of FIG. 25, it is obviously observed, in FIG. 25, that the absorption peak of C═O appears at 1740 cm$^{-1}$, indicating that the reactive functional group (OH group) contained in Flame Retardant 1 is reacted with epoxy group of GMA to produce C═O. Thus, it is confirmed that the reactive functional group contained in Flame Retardant 1 can be successfully reacted with epoxy group of GMA.

[Flame Retardancy Test of Flame Retardant Material]

The flame retardant of the present disclosure was uniformly mixed with methyl novolac epoxy resin (NPCN-704, epoxy equivalent 200-220 g/eq, purchased from Nan Ya Plastics) according to the weights shown in Table 1. Then, the mixture is injected into a mold, polymerized in an oven at a temperature of 190° C. for 12 hours, and naturally cooled to room temperature. The test specimen having dimensions of 5 inches length×0.5 inch width×1/16 inch thickness was removed from the mold. All test specimens were tested in the vertical position according to standard flame retardancy test procedure UL-94 (Safety certification of Underwriters Laboratories Inc.). The results are shown in Table 1.

TABLE 1

| Test Specimen | Flame Retardant/ weight (g) | Epoxy resin Weight (g) | Color of Test Specimen | t1 (s) | t2 (s) | Drip | UL94 Rating |
|---|---|---|---|---|---|---|---|
| 1 | Flame Retardant 1/40 | 36 | Black | 1.2 | 1.0 | No | V-0 |
| 2 | Flame Retardant 4/40 | 25.2 | Tan | 2.0 | 1.5 | No | V-0 |
| 3 | Flame Retardant 5/40 | 33.6 | Black | 0.1 | 0.1 | No | V-0 |
| 4 | Flame Retardant 6/40 | 18 | Transparent | 4.3 | 3.2 | No | V-0 |
| 5 | Flame Retardant 7/40 | 18 | Pale yellow | 5.0 | 4.2 | No | V-0 |

Note:
* t1: The regulated flame was placed onto a test specimen for 10 seconds and the time measured until the flame self extinguished was recorded as t1.
* t2: The regulated flame was placed onto the test specimen again for 10 seconds and removed, and the second burn time was recorded as t2.
* Drip: Whether a wad of cotton placed beneath the burning end of a test specimen is ignited by the drips from the test specimen.

[Detection and Analysis Method]

1. FT-IR Spectroscopy

The precursors and flame retardants disclosed in the above examples were each ground into powder and uniformly mixed with potassium bromide (KBr) powder to prepare a KBr disc for FT-IR measurement. Then, the analysis was carried out using a Fourier transform infrared spectrometer (Model: Spectrum one, available from Perkin Elmer).

2. Nuclear Magnetic Resonance (NMR) Spectroscopy

Structural analyses of the compounds were carried out using a $^1$H NMR spectrometer (Model: Inova-400, available from Varian UNITY). NMR spectra were recorded on 600 MHz in deuterated dimethyl sulfoxide (DMSO-d$_6$) solvent at room temperature. Multiplicities were reported as s, singlet; d, doublet; t, triplet, and m, multiplet.

The analysis results obtained by FT-IR spectroscopy and $^1$H NMR spectroscopy of the examples confirm that the flame retardant of the present disclosure contains at least one kind of reactive functional group (i.e. hydroxyl group and/or amino group). Further, the results of the reactivity test of the flame retardant confirm that the reactive functional group(s) (hydroxyl group and/or the amino group) in the structure of the flame retardant of the present disclosure is/are reactive and capable of reacting with a compound/polymer able to react with hydroxyl group or amino group, thereby expanding the applicability of the flame retardant of the present disclosure. Moreover, the flame retardancy test result of the flame retardant material proves that after the flame retardant of the present disclosure is mixed with a polymer and polymerized, the cured polymer exhibits excellent flame retardancy, V0 rating under UL-94 standard, and has no flaming drips during UL-94 testing.

What is claimed is:

1. A flame retardant, having a structure represented by the following Structural Formula (I) or (II):

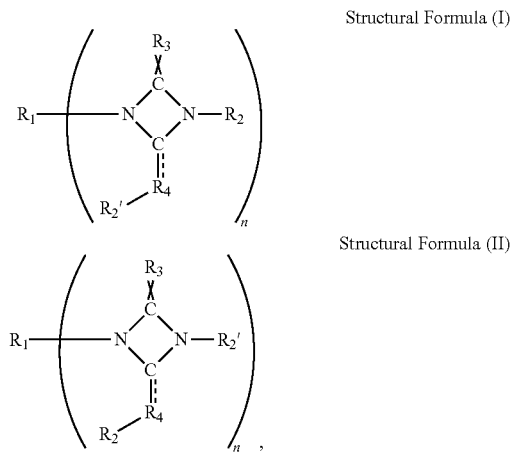

wherein

R$_1$ and R$_2$ each independently represent a substituted or unsubstituted aromatic group, a substituted or unsubstituted araliphatic group, a substituted or unsubstituted aliphatic group, or a substituted or unsubstituted cycloaliphatic group; R$_2$' is R$_2$-(-N=C=N-R$_5$-)$_m$, wherein R$_5$ is arylene or alkylene and is identical or different in the repeat unit, and m is an integer from 0 to 5;

n is an integer equal to or larger than 1;

">=<" and "====" respectively represent either a double bond or two single bonds, and ">=<" and "====" are not both double bonds;

when ">=<" represents a double bond, R$_3$ is an oxygen atom;

when ">=<" represents two single bonds, R$_3$ is R$_{3a}$ and R$_{3b}$, wherein R$_{3a}$ is a hydroxyl group, and R$_{3b}$ is

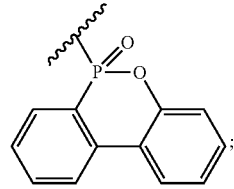 [SMILES: *P1(=O)Oc2ccccc2-c2ccccc21]

when "====" represents a double bond, R$_4$ is an nitrogen atom; and when "====" represents two single bonds, R$_4$ is R$_{4a}$ and R$_{4b}$, wherein R$_{4a}$ is a secondary amino group, and R$_{4b}$ is

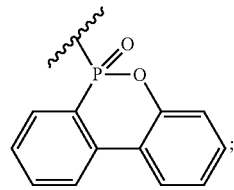 [SMILES: *P1(=O)Oc2ccccc2-c2ccccc21]

and R$_2$' is attached to R$_{4a}$ in Structural Formula (I), and R$_2$ is attached to R$_{4a}$ in Structural Formula (II).

2. The flame retardant according to claim 1, wherein n is an integer from 1 to 4.

3. The flame retardant according to claim 1, wherein n is an integer from 1 to 3.

4. The flame retardant according to claim 1, wherein R$_1$ is a substituted or unsubstituted aryl or aralkyl group having 6 to 20 carbon atoms, a substituted or unsubstituted alkyl group having 1 to 18 carbon atoms, or a substituted or unsubstituted cycloalkyl group having 6 to 16 carbon atoms.

5. The flame retardant according to claim 4, wherein R$_1$ is a substituted or unsubstituted aryl group having 6 to 18 carbon atoms, a substituted or unsubstituted aralkyl group having 6 to 15 carbon atoms, a substituted or unsubstituted alkyl group having 1 to 10 carbon atoms, or a substituted or unsubstituted cycloalkyl group having 6 to 10 carbon atoms.

6. The flame retardant according to claim 5, wherein R$_1$ is an unsubstituted aryl group having 6 to 14 carbon atoms, an unsubstituted aralkyl group having 6 to 13 carbon atoms, an unsubstituted alkyl group having 1 to 6 carbon atoms, or an unsubstituted cycloalkyl group having 6 to 8 carbon atoms.

7. The flame retardant according to claim 1, wherein R$_2$ is a substituted or unsubstituted aryl or aralkyl group having 6 to 20 carbon atoms, a substituted or unsubstituted alkyl group having 1 to 18 carbon atoms, or a substituted or unsubstituted cycloalkyl group having 6 to 16 carbon atoms.

8. The flame retardant according to claim 7, wherein R$_2$ is a substituted or unsubstituted aryl group having 6 to 18 carbon atoms, a substituted or unsubstituted aralkyl group having 6 to 15 carbon atoms, a substituted or unsubstituted alkyl group having 1 to 10 carbon atoms, or a substituted or unsubstituted cycloalkyl group having 6 to 10 carbon atoms.

9. The flame retardant according to claim 8, wherein R$_2$ is an unsubstituted aryl group having 6 to 14 carbon atoms, an unsubstituted aralkyl group having 6 to 13 carbon atoms, an unsubstituted alkyl group having 1 to 6 carbon atoms, or an unsubstituted cycloalkyl group having 6 to 8 carbon atoms.

10. The flame retardant according to claim 1, wherein $R_5$ is an alkylene group having 1 to 24 carbon atoms or an arylene group having 6 to 22 carbon atoms.

\* \* \* \* \*